(12) United States Patent
Masuda et al.

(10) Patent No.: US 9,232,972 B2
(45) Date of Patent: Jan. 12, 2016

(54) GRASPING TREATMENT DEVICE

(71) Applicant: OLYMPUS CORPORATION, Tokyo (JP)

(72) Inventors: Shinya Masuda, Hino (JP); Ryu Onuma, Tama (JP); Tomoyuki Kaga, Hachioji (JP); Genri Inagaki, Maplegrove, MN (US)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/071,059

(22) Filed: Nov. 4, 2013

(65) Prior Publication Data

US 2014/0135762 A1    May 15, 2014

Related U.S. Application Data

(63) Continuation of application No. PCT/JP2013/057712, filed on Mar. 18, 2013.

(60) Provisional application No. 61/612,632, filed on Mar. 19, 2012.

(51) Int. Cl.
*A61B 18/04* (2006.01)
*A61B 17/28* (2006.01)
(Continued)

(52) U.S. Cl.
CPC ......... *A61B 18/04* (2013.01); *A61B 17/320092* (2013.01); *A61B 18/1445* (2013.01);
(Continued)

(58) Field of Classification Search
CPC ................ A61B 18/1447; A61B 2017/294; A61B 2017/2944; A61B 2017/2947; A61B 17/320092

USPC .................................... 606/206, 207
See application file for complete search history.

(56) References Cited

U.S. PATENT DOCUMENTS

| | | | |
|---|---|---|---|
| 6,569,178 B1 | 5/2003 | Miyawaki et al. | |
| 2007/0043352 A1* | 2/2007 | Garrison et al. | 606/51 |

(Continued)

FOREIGN PATENT DOCUMENTS

| | | |
|---|---|---|
| EP | 2 263 586 A2 | 12/2010 |
| JP | A-2000-254135 | 9/2000 |

(Continued)

OTHER PUBLICATIONS

International Search Report issued in International Application No. PCT/JP2013/057712 dated Apr. 16, 2013 (with translation).

(Continued)

*Primary Examiner* — Ronald Hupczey
*Assistant Examiner* — Bo Ouyang
(74) *Attorney, Agent, or Firm* — Oliff PLC

(57) ABSTRACT

A grasping treatment device includes a probe including a first electrode portion in its distal portion, and a jaw configured to open or close relative to the first electrode portion and including a second electrode portion. The grasping treatment device includes a grasping force converting unit converting a grasping force so that a second grasping force between the distal portion of the probe and the jaw in a second treatment mode in which high-frequency current alone is transmitted to the first electrode portion and the second electrode portion is greater than a first grasping force between the distal portion of the probe and the jaw in a first treatment mode in which at least an ultrasonic vibration is transmitted to the distal portion of the probe.

6 Claims, 24 Drawing Sheets

(51) Int. Cl.
*A61B 17/32* (2006.01)
*A61B 18/14* (2006.01)
*A61N 7/00* (2006.01)
A61B 18/00 (2006.01)
A61B 17/00 (2006.01)
A61B 17/29 (2006.01)

(52) U.S. Cl.
CPC ........ *A61N 7/00* (2013.01); *A61B 2017/00367* (2013.01); *A61B 2017/2825* (2013.01); *A61B 2017/2929* (2013.01); *A61B 2017/2946* (2013.01); *A61B 2018/00589* (2013.01); *A61B 2018/00994* (2013.01)

(56) References Cited

U.S. PATENT DOCUMENTS

| | | | |
|---|---|---|---|
| 2008/0132887 A1 | 6/2008 | Masuda et al. | |
| 2009/0054894 A1* | 2/2009 | Yachi | 606/42 |
| 2009/0088668 A1 | 4/2009 | Masuda | |
| 2009/0270853 A1 | 10/2009 | Yachi et al. | |
| 2011/0004127 A1 | 1/2011 | Okada et al. | |
| 2011/0071523 A1* | 3/2011 | Dickhans | 606/45 |
| 2012/0022526 A1* | 1/2012 | Aldridge et al. | 606/45 |
| 2012/0277778 A1 | 11/2012 | Masuda et al. | |

FOREIGN PATENT DOCUMENTS

| | | |
|---|---|---|
| JP | 2001-514541 | 9/2001 |
| WO | WO 2011/099571 A1 | 8/2011 |

OTHER PUBLICATIONS

International Preliminary Report on Patentability issued in International Application No. PCT/JP2013/057712 dated Oct. 2, 2014 (translation only).

Office Action issued in Japanese Application No. 2013-544051 mailed Jan. 7, 2014 (with translation).

Oct. 16, 2015 Search Report issued in European Patent Application No, 13764334.2.

* cited by examiner

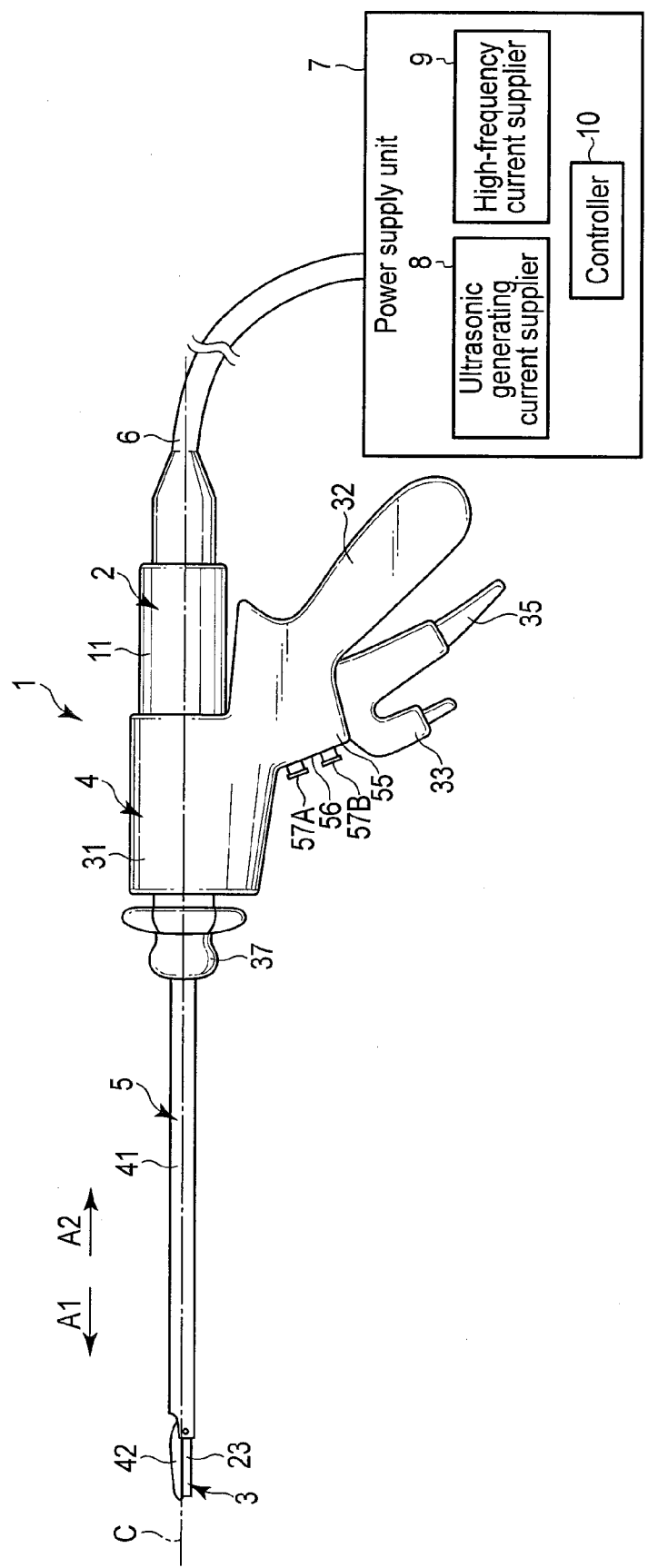
F I G. 1

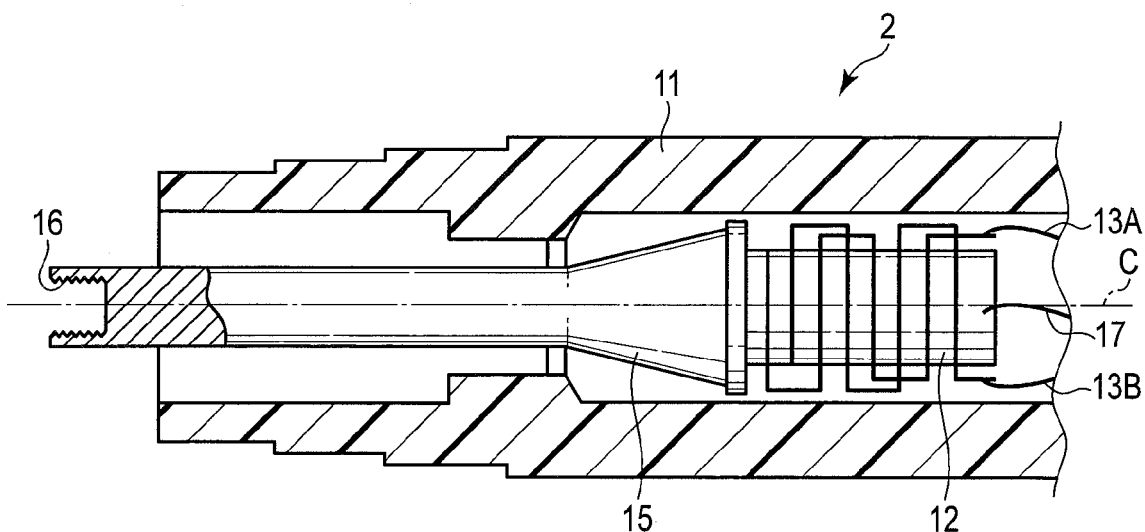
F I G. 2
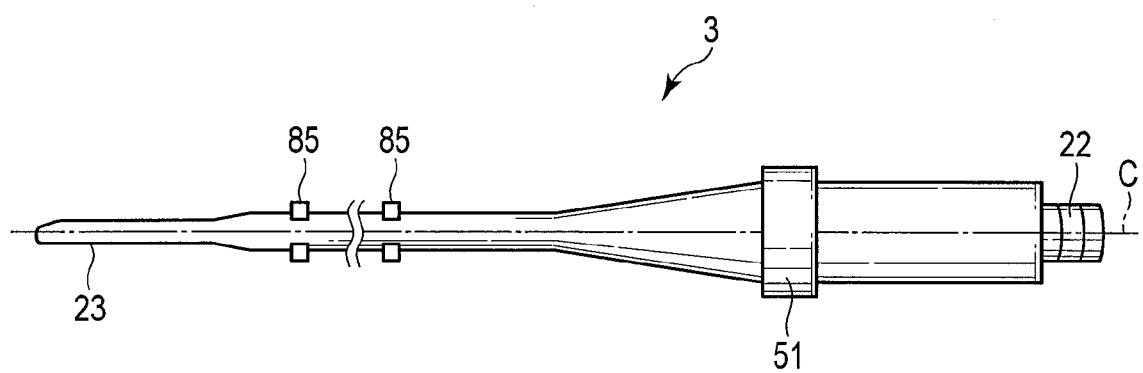
F I G. 3

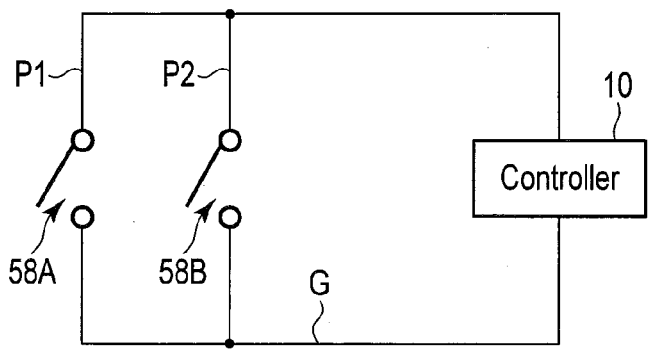
F I G. 7
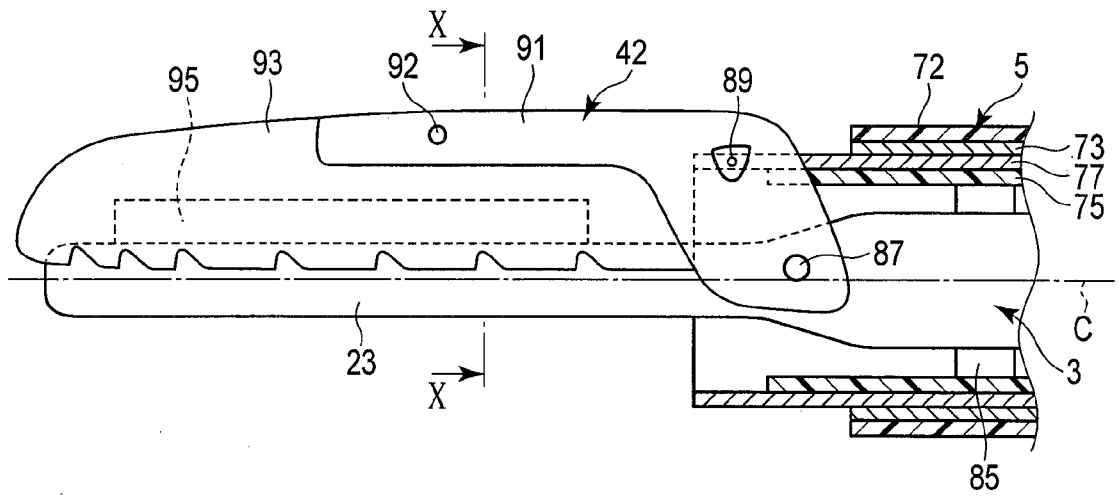
F I G. 8
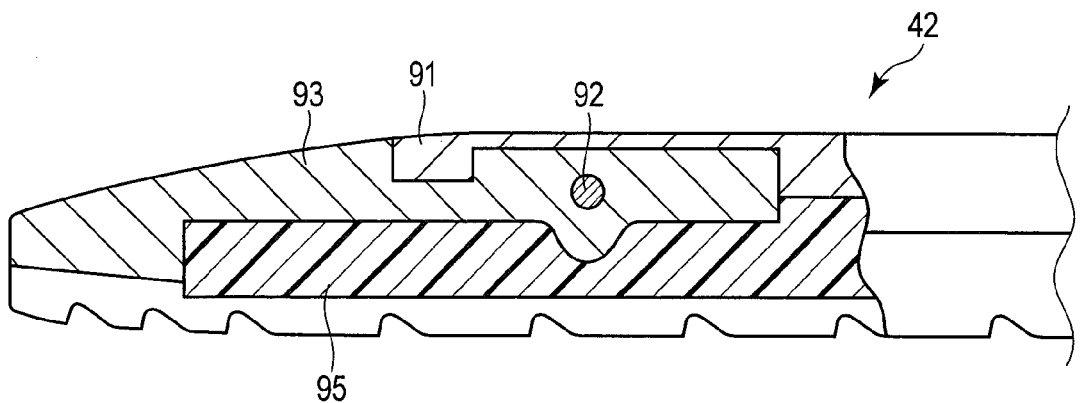
F I G. 9

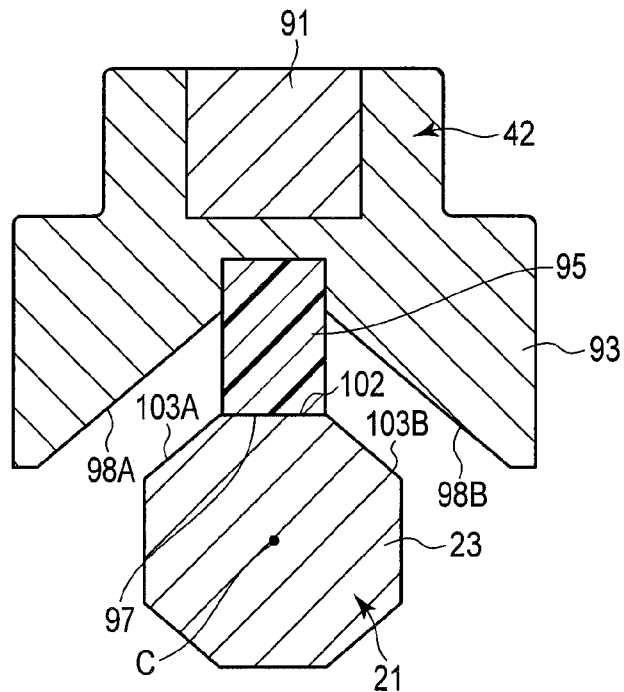
F I G. 10
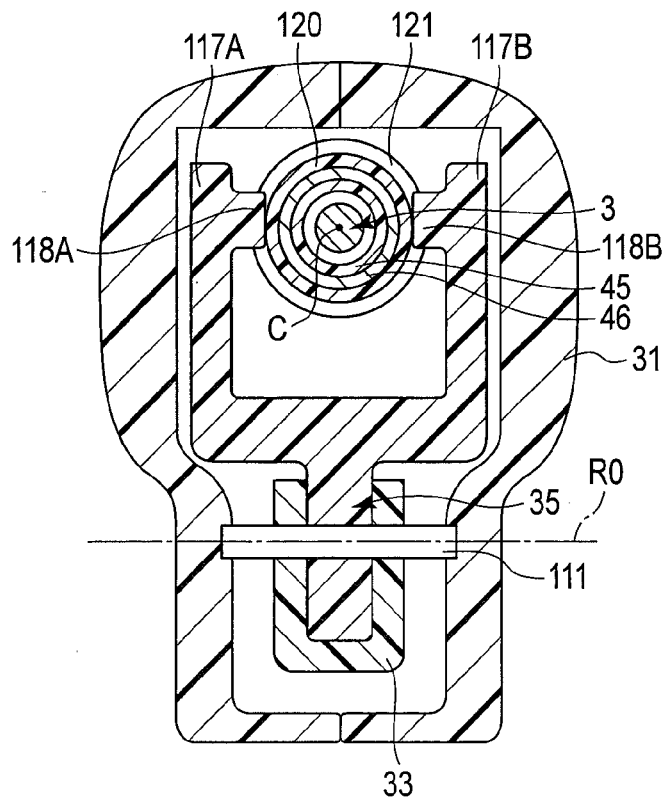
F I G. 11

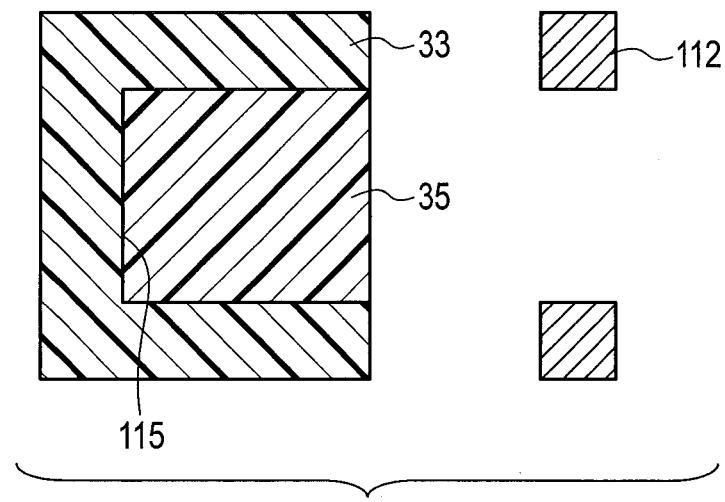
F I G. 12A
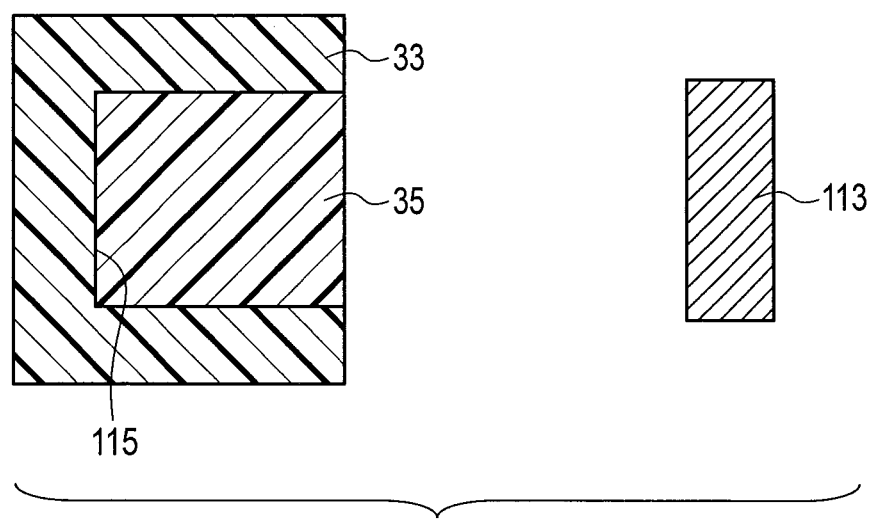
F I G. 12B

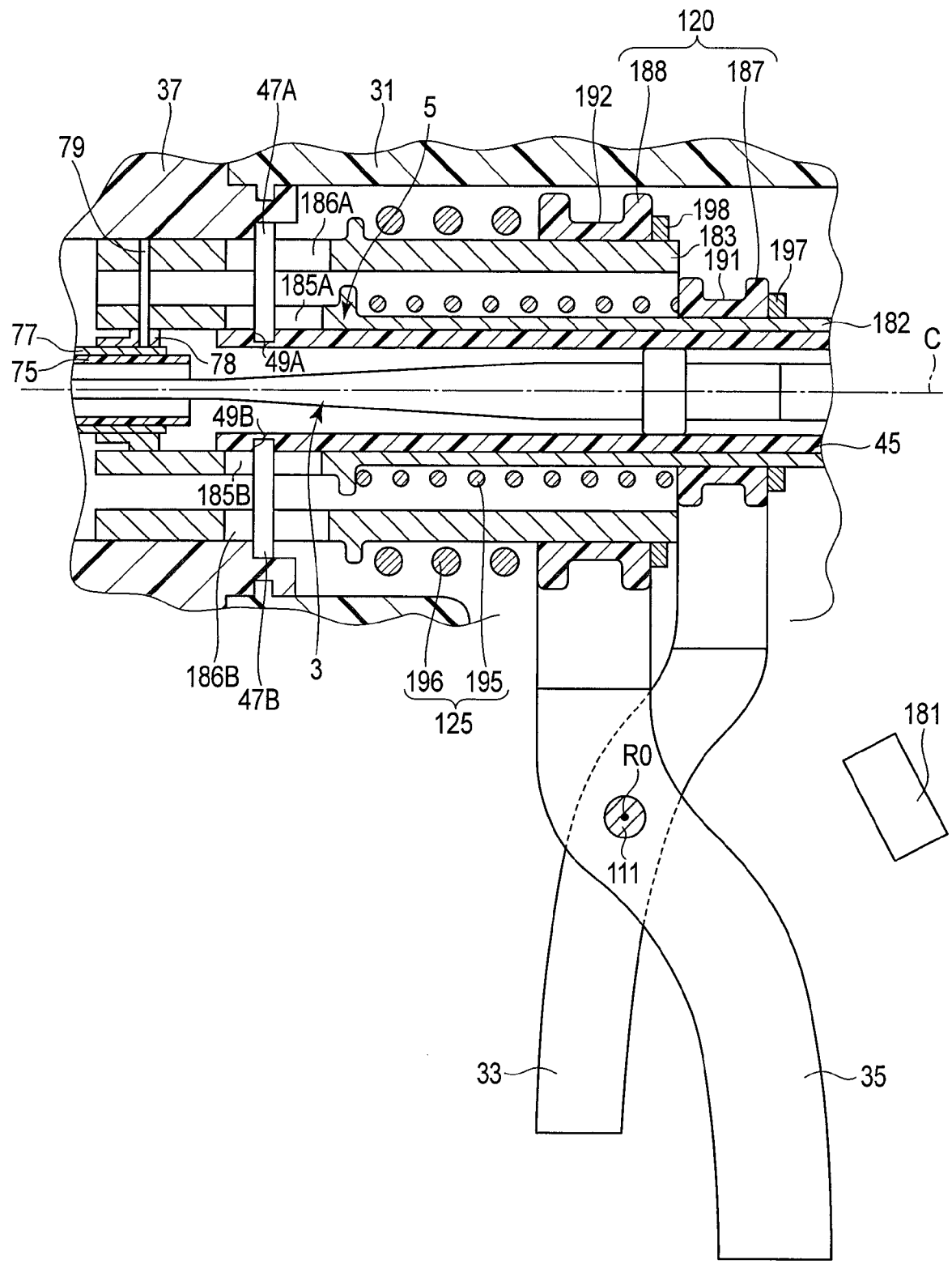
F I G. 22

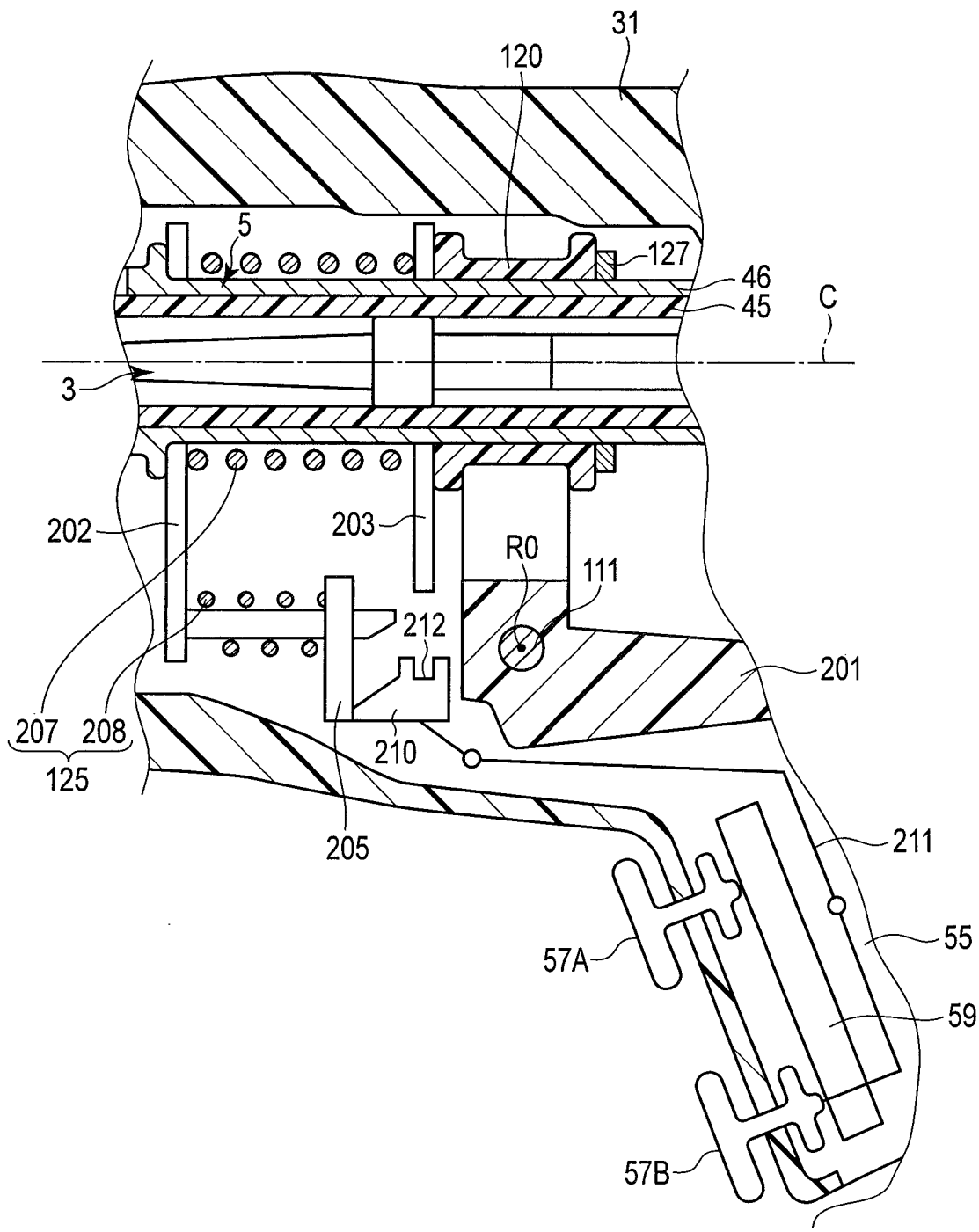
F I G. 24

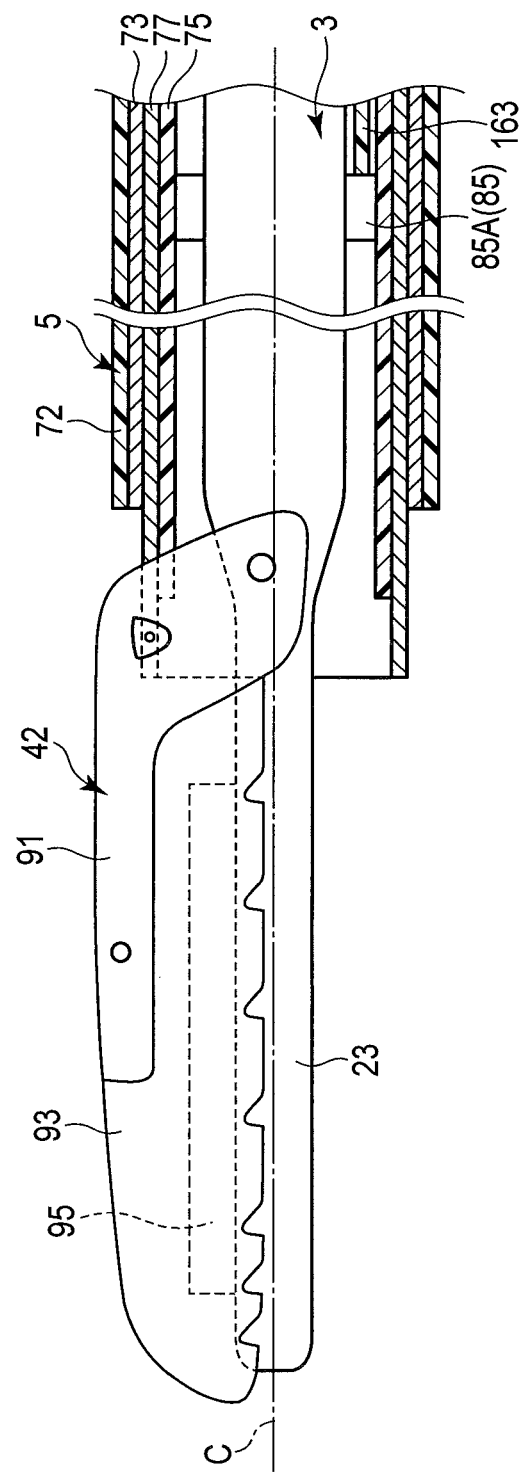
F I G. 27

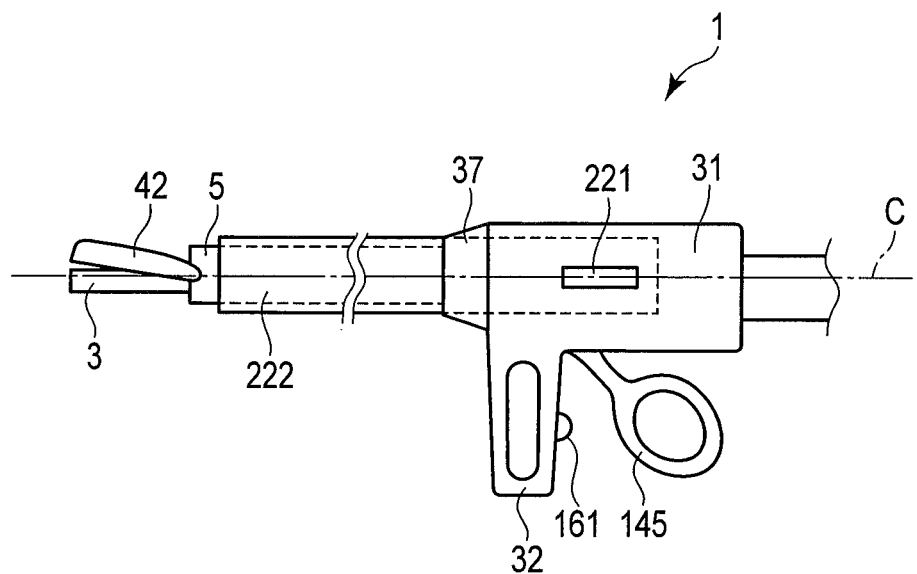
F I G. 32
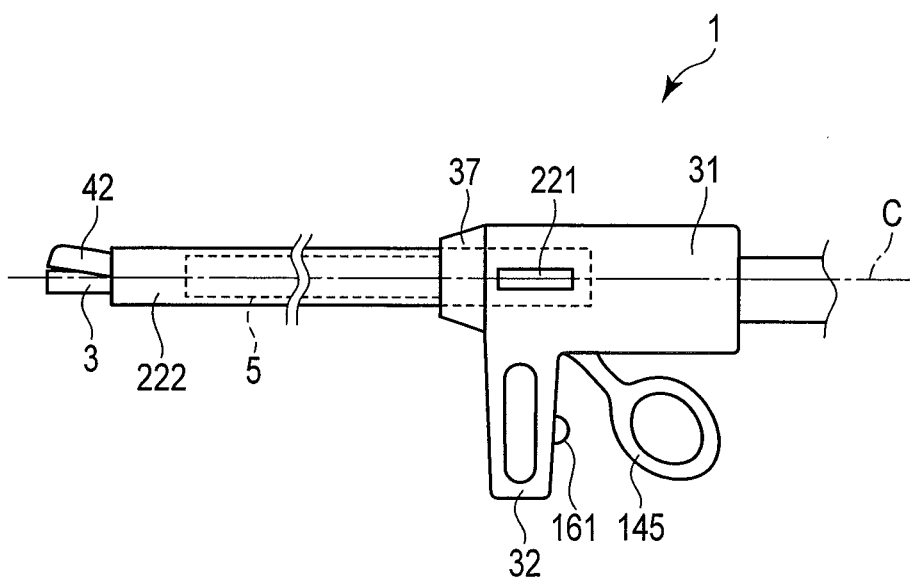
F I G. 33

GRASPING TREATMENT DEVICE

CROSS-REFERENCE TO RELATED APPLICATIONS

This is a Continuation application of PCT Application No. PCT/JP2013/057712, filed Mar. 18, 2013 and based upon and claiming the benefit of priority from prior U.S. Provisional Application No. 61/612,632, filed Mar. 19, 2012, the entire contents of which are incorporated herein by reference.

BACKGROUND OF THE INVENTION

1. Field of the Invention

The present invention relates to a grasping treatment device which is configured to grasp a grasping target such as a living tissue between a distal portion of a probe and a jaw configured to open or close relative to the distal portion of the probe, and which is configured to treat the living tissue by using, for example, an ultrasonic vibration and a high-frequency current.

2. Description of the Related Art

US 2009/0270853, US 2009/0088668, and US 2008/132887 each disclose a grasping treatment device which includes a probe including a first electrode portion provided in its distal portion, and a jaw configured to open or close relative to the first electrode portion. In each of the grasping treatment devices, the probe is configured to transmit an ultrasonic vibration from a proximal direction to a distal direction, and the ultrasonic vibration is transmitted to the first electrode portion. A high-frequency current is transmitted to the first electrode portion of the probe through the probe. The probe is inserted through a sheath, and the probe is electrically insulated from the sheath. The jaw is attached to a distal portion of the sheath. The jaw includes an abutting portion configured to abut on the first electrode portion when the jaw is closed relative to the first electrode portion, and a second electrode portion having a clearance between the first electrode portion and the second electrode portion when the abutting portion is in abutment with the first electrode portion. The abutting portion of the jaw is made of an insulating material. A high-frequency current is transmitted to the second electrode portion through the sheath.

In a first treatment mode which is one treatment mode, the ultrasonic vibration is transmitted to the first electrode portion (the distal portion of the probe) when a living tissue such as a blood vessel is grasped between the first electrode portion and the jaw. At the same time, a high-frequency current is transmitted to the first electrode portion and the second electrode portion. The probe is ultrasonically vibrated while the grasping target living tissue is grasped between the first electrode portion and the jaw, and frictional heat is thereby generated between the first electrode portion and the living tissue. The living tissue is simultaneously cut open and coagulated between the first electrode portion and the jaw by the generated frictional heat. At the same time, a high-frequency current runs through the living tissue grasped between the first electrode portion and the second electrode portion. The living tissue is reformed by the high-frequency current, and the coagulation of the living tissue is accelerated. In a second treatment mode different from the first treatment mode, a high-frequency current alone is transmitted to the first electrode portion and the second electrode portion while a living tissue such as a blood vessel is grasped between the first electrode portion and the jaw. At the same time, a high-frequency current runs through the living tissue grasped between the first electrode portion and the second electrode portion, and the living tissue is only coagulated.

BRIEF SUMMARY OF THE INVENTION

According to one aspect of the invention, a grasping treatment device includes that: a probe which extends along a longitudinal axis, and which is configured to transmit an ultrasonic vibration from a proximal direction to a distal direction, the probe including, in its distal portion, a first electrode portion which functions as an electrode when a high-frequency current is transmitted thereto through the probe; a jaw configured to open or close relative to the first electrode portion, the jaw including a second electrode portion which functions as an electrode when a high-frequency current is transmitted thereto; an open-or-close operation input portion configured to perform an open-or-close operation of the jaw and the distal portion of the probe; and a grasping force converting unit configured to convert a grasping force so that a second grasping force between the distal portion of the probe and the jaw in a second treatment mode in which the high-frequency current alone is transmitted to the first electrode portion and the second electrode portion is greater than a first grasping force between the distal portion of the probe and the jaw in a first treatment mode in which at least the ultrasonic vibration is transmitted to the distal portion of the probe.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing a grasping treatment device according to a first embodiment of the present invention;

FIG. 2 is a schematic sectional view showing the configuration of a vibrator unit (oscillator unit) according to the first embodiment;

FIG. 3 is a schematic side view showing the configuration of a probe according to the first embodiment;

FIG. 7 is a circuit diagram showing an electric connection state between a first switch portion, a second switch portion, and a controller according to the first embodiment;

FIG. 8 is a partly sectional schematic view showing the configurations of a distal portion of the probe, a distal portion of a sheath, and a jaw according to the first embodiment;

FIG. 9 is a partly sectional schematic side view showing the jaw according to the first embodiment;

FIG. 10 is a sectional view taken along the line X-X in FIG. 8;

FIG. 11 is a sectional view taken along the line 11-11 in FIG. 4;

FIG. 12A is a sectional view taken along the line 12A-12A in FIG. 4;

FIG. 12B is a sectional view taken along the line 12B-12B in FIG. 4;

FIG. 22 is a schematic sectional view showing a coupling configuration between a handle unit and a sheath according to a third embodiment of the present invention;

FIG. 24 is a schematic sectional view showing the internal configuration of the handle unit according to a modification of the third embodiment in the first treatment mode;

FIG. 27 is a partly sectional schematic view showing the configurations of a distal portion of a probe, a distal portion of a sheath, and a jaw according to the fourth embodiment in the first treatment mode;

FIG. 32 is a schematic view showing a grasping treatment device according to a fifth embodiment of the present invention in the first treatment mode; and FIG. 33 is a schematic view showing the grasping treatment device according to the fifth embodiment in the second treatment mode.

DETAILED DESCRIPTION OF THE INVENTION

First Embodiment

Figure 4:
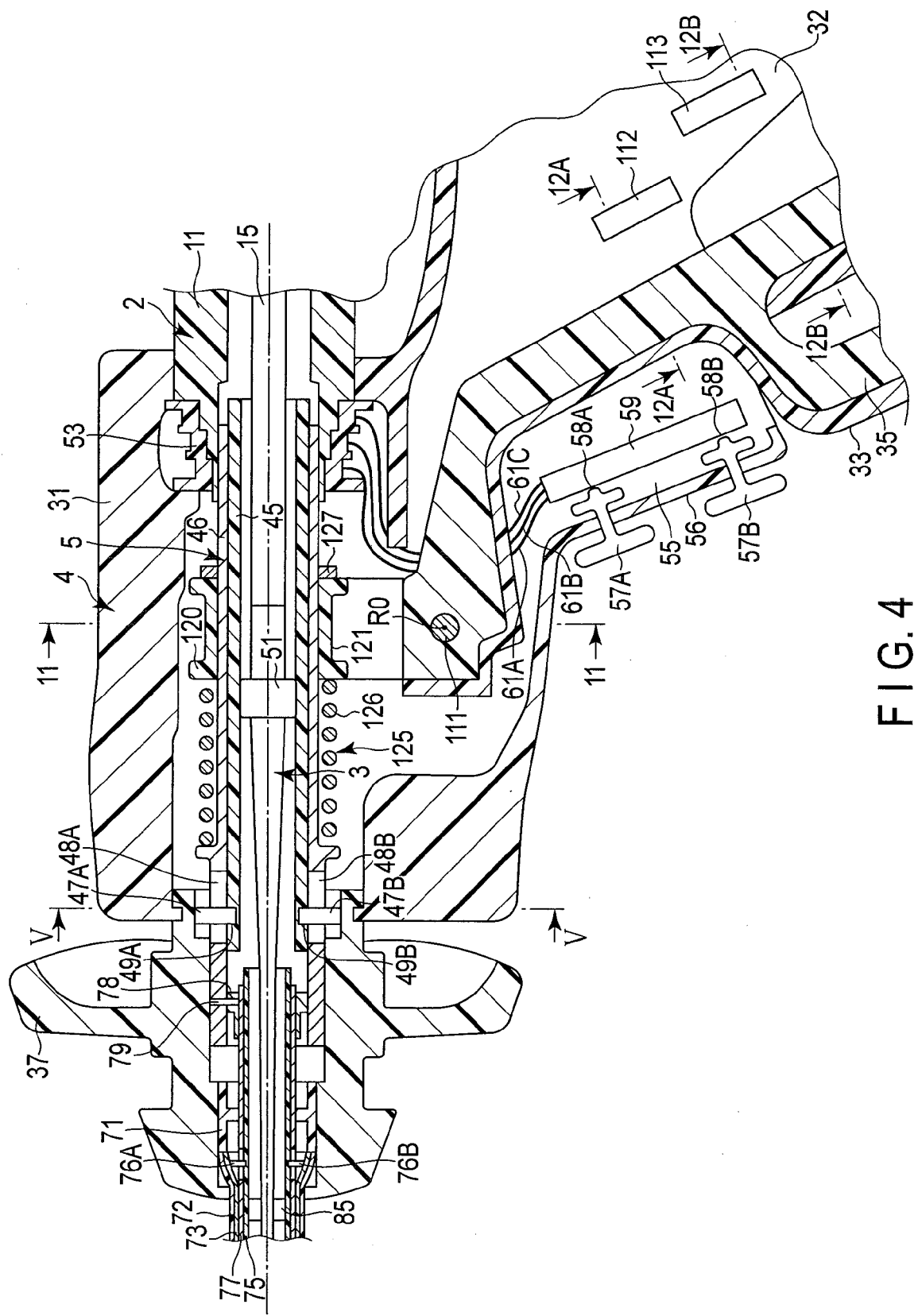
FIG. 4 is a schematic sectional view showing the internal configuration of a handle unit according to the first embodiment.

A first embodiment of the present invention is described with reference to FIG. 1 to FIG. 14B. FIG. 1 is a schematic view showing a grasping treatment device 1 according the present embodiment. As shown in FIG. 1, the grasping treatment device 1 has a longitudinal axis C. Here, one of two directions parallel to the longitudinal axis C is a distal direction (direction of an arrow A1 in FIG. 1), and the direction opposite to the distal direction is a proximal direction (direction of an arrow A2 in FIG.

The grasping treatment device 1, which is a surgical treatment device, includes a vibrator unit (oscillator unit) 2, a probe 3, a handle unit 4, and a sheath 5. The vibrator unit 2 includes a vibrator case (oscillator case) 11. One end of a cable 6 is connected to a proximal end of the vibrator case 11. The other end of the cable 6 is connected to a power supply unit 7. The power supply unit 7 includes an ultrasonic generating current supplier 8, a high-frequency current supplier 9, and a controller 10. The grasping treatment device 1 and the power supply unit 7 constitute a surgical treatment system.

FIG. 2 is a diagram showing the configuration of the vibrator unit 2. As shown in FIG. 2, an ultrasonic vibrator (ultrasonic oscillator) 12 including piezoelectric elements, which is configured to convert a current to an ultrasonic vibration, is provided in the vibrator case 11. One end of each of electric signal lines 13A and 13B is connected to the ultrasonic vibrator 12. Each of the electric signal lines 13A and 13B has the other end connected to the ultrasonic generating current supplier 8 of the power supply unit 7 through an inside of the cable 6. The ultrasonic vibration is generated in the ultrasonic vibrator 12 by a supply of a current to the ultrasonic vibrator 12 from the ultrasonic generating current supplier 8 via the electric signal lines 13A and 13B. A columnar horn 15 which is configured to increase amplitude of the ultrasonic vibration is coupled to the distal direction side of the ultrasonic vibrator 12.

The horn 15 is supported by the vibrator case 11, and is electrically insulated from the vibrator case 11. An internal thread 16 is formed in a distal portion of the horn 15. In addition to the electric signal lines 13A and 13B, an electric signal line 17 which extends from the high-frequency current supplier 9 of the power supply unit 7 through the inside of the cable 6 is connected to the ultrasonic vibrator 12.

FIG. 3 is a diagram showing the configuration of the probe 3. As shown in FIG. 3, the probe 3 is formed into a columnar shape along the longitudinal axis C. The longitudinal axis C of the grasping treatment device 1 passes through an axial center of the probe 3. An external thread 22 is provided in a proximal-direction side part of the probe 3. When the external thread 22 of the probe 3 is screwed to the internal thread 16 of horn 15, the ultrasonic probe 3 is attached to the horn 15.

When the probe 3 is attached to the horn 15, the ultrasonic vibration generated in the ultrasonic vibrator 12 can be transmitted to a distal portion of the ultrasonic probe 3 via the horn 15. That is, the probe 3 can transmit the ultrasonic vibration from the proximal direction to the distal direction. A first electrode portion 23 is provided in the distal portion of the probe 3. When the probe 3 is attached to the horn 15, a high-frequency current can be transmitted to the first electrode portion 23 from the high-frequency current supplier 9 through the electric signal line 17, the ultrasonic vibrator 12, the horn 15, and the probe 3. When the high-frequency current is transmitted to the first electrode portion 23, the first electrode portion 23 has a first electric potential E1.

As shown in FIG. 1, the handle unit 4 includes a cylindrical case 31 extending along the longitudinal axis C. The cylindrical case 31 is made of an insulating material. A fixed handle 32 extends from the cylindrical case 31 in a direction tilted (inclined) relative to the longitudinal axis C. The fixed handle 32 is formed integrally with the cylindrical case 31. A first movable handle 33 and a second movable handle 35 are rotatably attached to the cylindrical case 31. The first movable handle 33 and the second movable handle 35 are configured to open or close relative to the fixed handle 32 substantially in parallel with the longitudinal axis C. The first movable handle 33 and the second movable handle 35 are located to the distal direction side of the fixed handle 32.

The vibrator unit 2 is coupled to the cylindrical case 31 from the proximal direction side, and the sheath 5 is coupled to the cylindrical case 31 from the distal direction side. The probe 3 is inserted into the cylindrical case 31 from the distal direction side, and the probe 3 is inserted through the sheath 5. A jaw 42 is rotatably (pivotably) attached to a distal portion of the sheath 5. The jaw 42 is configured to open or close relative to the first electrode portion 23 of the probe 3. The jaw 42 is opened or closed relative to the first electrode portion 23 by the first movable handle 33 and the second movable handle 35. That is, the first movable handle 33 is a part of an open-or-close operation input portion configured to perform an open-or-close operation of the jaw 42, and the second movable handle 35 is a part of the open-or-close operation input portion configured to perform the open-or-close operation of the jaw 42.

The handle unit 4 also includes a rotational operation knob 37 which is a rotational operation input portion and which is coupled to the distal direction side of the cylindrical case 31. The rotational operation knob 37 is coupled to the cylindrical case 31 rotatably in directions around the longitudinal axis. When the rotational operation knob 37 rotates relative to the cylindrical case 31, the vibrator unit 2, the probe 3, the sheath 5, and the jaw 42 rotate relative to the cylindrical case 31 in one of the directions around the longitudinal axis.

FIG. 4 is a diagram showing the internal configuration of the handle unit 4. As shown in FIG. 4, the probe 3 and the sheath 5 extend into the cylindrical case 31 along the longitudinal axis C through an inside of the rotational operation knob 37. A proximal end of the probe 3 is attached to the horn 15 inside the cylindrical case 31. As a result, the vibrator unit 2 is coupled to the probe 3. A proximal portion of the sheath 5 is coupled to the vibrator case 11 inside the cylindrical case 31. As a result, the vibrator unit 2 is coupled to the sheath 5.

A connection cylindrical member 45 which couples the probe 3 to the sheath 5 is provided inside the cylindrical case 31 of the handle unit 4. The sheath 5 includes a movable cylindrical member 46 provided to an outer peripheral direction side of the connection cylindrical member 45. The connection cylindrical member 45 and the movable cylindrical member 46 are provided along the longitudinal axis C. The connection cylindrical member 45 is made of an insulating material such as a resin. The movable cylindrical member 46 is made of an electrically conducting material such as a metal.

Figure 5:
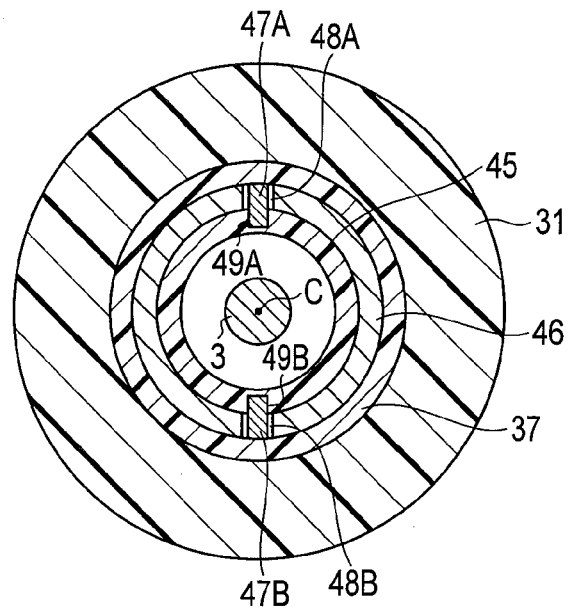
FIG. 5 is a sectional view taken along the line V-V in FIG. 4.

FIG. 5 is a sectional view taken along the line V-V in FIG. 4. As shown in FIG. 4 and FIG. 5, engaging pins 47A and 47B are fixed to the rotational operation knob 37 so that these engaging pins 47A and 47B are located apart from each other in the directions around the longitudinal axis. The engaging pins 47A and 47B protrude in an inner peripheral direction from an inner peripheral portion of the rotational operation knob 37. Through-holes 48A and 48B are provided in the movable cylindrical member 46 so that these through-holes 48A and 48B are located apart from each other in the directions around the longitudinal axis. Each of the through-holes 48A and 48B is formed into the shape of a long hole along the longitudinal axis C, and passes through the movable cylindrical member 46 in diametrical directions. The connection cylindrical member 45 is provided with engaging depressions 49A and 49B that are depressed toward the inner peripheral direction. The engaging depressions 49A and 49B are provided apart from each other in the directions around the longitudinal axis.

The engaging pin 47A is inserted through the through-hole 48A, and is engaged with the engaging depression 49A. The engaging pin 47B is inserted through the through-hole 48B, and is engaged with the engaging depression 49B. When each of the engaging pins 47A and 47B is engaged with the corresponding engaging depression 49A or 49B, the connection cylindrical member 45 is fixed to the rotational operation knob 37. When each of the engaging pins 47A and 47B is inserted through the corresponding through-hole 48A or 48B, the movable cylindrical member 46 and the rotational operation knob 37 are regulated unrotatably relative to each other in the directions around the longitudinal axis. However, as each of the through-holes 48A and 48B is formed into the shape of a long hole along the longitudinal axis C, the movable cylindrical member 46 is movable relative to the rotational operation knob 37 and the connection cylindrical member 45 along the longitudinal axis C. According to the configuration described above, the connection cylindrical member 45 and the movable cylindrical member 46 are rotatable relative to the cylindrical case 31 together with the rotational operation knob 37 in the directions around the longitudinal axis. Moreover, the movable cylindrical member 46 is movable relative to the probe 3 and the handle unit 4 along the longitudinal axis C.

An elastic member 51 made of an insulating material is fixed to an outer peripheral portion of a proximal portion of the probe 3 (see FIG. 3). When the probe 3 is coupled to the horn 15, the elastic member 51 is located at a node position of the ultrasonic vibration. The elastic member 51 is pressed in the inner peripheral direction by an inner peripheral portion of the connection cylindrical member 45, and is contracted. The probe 3 is fixed to the connection cylindrical member 45 by the contraction of the elastic member 51. As a result, the probe 3 is coupled to the sheath 5 by the connection cylindrical member 45 and the elastic member 51.

When the rotational operation knob 37 is rotated in one of the directions around the longitudinal axis, a rotational drive force from the rotational operation knob 37 is transmitted to the probe 3 via the connection cylindrical member 45 and the elastic member 51. Consequently, the probe 3 can rotate relative to the cylindrical case 31 together with the rotational operation knob 37 and the connection cylindrical member 45. Since the connection cylindrical member 45 and the elastic member 51 are made of an insulating material, the probe 3 is electrically insulated from the movable cylindrical member 46.

As shown in FIG. 4, the movable cylindrical member 46 and the vibrator case 11 are engaged with each other so that the movable cylindrical member 46 is inserted into the vibrator case 11 in a coupling portion of the sheath 5 and the vibrator unit 2. The rotation of the movable cylindrical member 46 and the vibrator case 11 relative to each other in the directions around the longitudinal axis is regulated. However, the movable cylindrical member 46 is movable relative to the vibrator case 11 along the longitudinal axis C.

An electric connection ring 53 is provided to the outer peripheral direction side of the vibrator case 11 in a coupling portion of the sheath 5 and the vibrator case 11. The electric connection ring 53 is provided so that the electric connection ring 53 is fixed to the cylindrical case 31 of the handle unit 4. When the vibrator case 11 is coupled to the sheath 5 (movable cylindrical member 46), an outer peripheral portion of a distal portion of the vibrator case 11 is in contact with the electric connection ring 53, and an inner peripheral portion of the distal portion of the vibrator case 11 is in contact with the movable cylindrical member 46. The vibrator case 11 and the sheath 5 are rotatable together relative to the electric connection ring 53 in the directions around the longitudinal axis.

A switch arrangement portion 55 is provided between the cylindrical case 31 and the fixed handle 32. The switch arrangement portion 55 is formed integrally with the cylindrical case 31 and the fixed handle 32. The switch arrangement portion 55 includes a flat portion 56 substantially perpendicular to the longitudinal axis C. The flat portion 56 is provided on the side where the fixed handle 32, the first movable handle 33, and the second movable handle 35 are located if the longitudinal axis C is a center. The flat portion 56 is located to the distal direction side of the first movable handle 33 and the second movable handle 35.

A first treatment mode input button 57A which is a first treatment mode input portion and a second treatment mode input button 57B which is a second treatment mode input portion are provided on (in) the flat portion 56. When the first treatment mode input button 57A is pressed, an input operation of switching to a first treatment mode is performed. When the second treatment mode input button 57B is pressed, an input operation of switching to a second treatment mode is performed. A first switch portion 58A, a second switch portion 58B, and an electric circuit substrate 59 are provided in the switch arrangement portion 55. The first switch portion 58A is turned on or off by the input operation in the first treatment mode input button 57A. Similarly, the second switch portion 58B is turned on or off by the input operation in the second treatment mode input button 57B.

Figure 6:
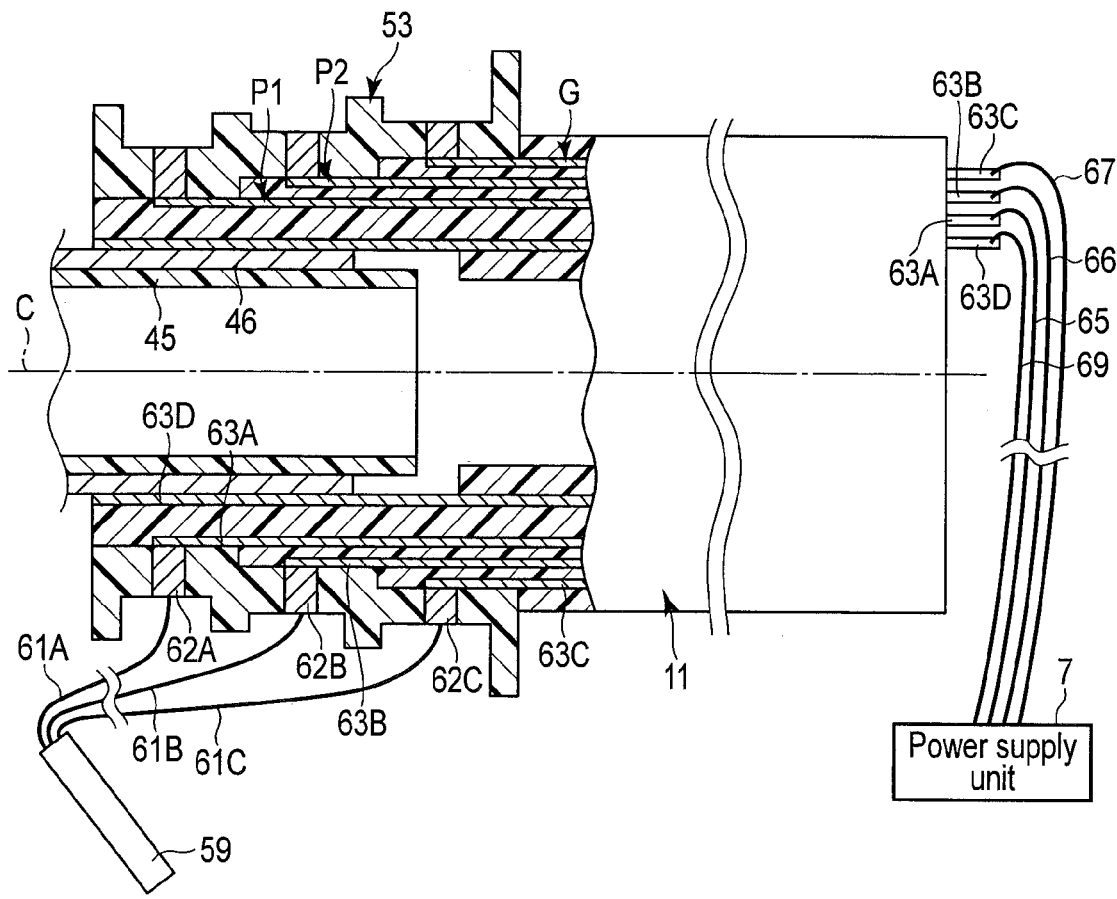
FIG. 6 is a schematic view showing an electric connection state in a vibrator case (oscillator case) according to the first embodiment.

FIG. 6 is a schematic view showing an electric connection state in the vibrator case 11. As shown in FIG. 4 and FIG. 6, three electric signal lines 61A to 61C are provided in the cylindrical case 31. The electric signal line 61A is electrically connected to the first switch portion 58A via an electric circuit on the electric circuit substrate 59. The electric signal line 61B is electrically connected to the second switch portion 58B via the electric circuit on the electric circuit substrate 59. The electric signal line 61C is electrically connected to the first switch portion 58A and the second switch portion 58B via the electric circuit on the electric circuit substrate 59. The electric signal line 61C is a common line shared as a ground line of the first switch portion 58A and the second switch portion 58B.

The electric connection ring 53 includes a first electric connection portion 62A, a second electric connection portion 62B, and a third electric connection portion 62C. The first electric connection portion 62A is electrically insulated from the second electric connection portion 62B. The second electric connection portion 62B is electrically insulated from the third electric connection portion 62C. The first electric connection portion 62A is electrically insulated from the third electric connection portion 62C. The electric signal line 61A is connected to the first electric connection portion 62A. The electric signal line 61B is connected to the second electric connection portion 62B. The electric signal line 61C is connected to the third electric connection portion 62C.

The vibrator case 11 includes a first electric conducting portion 63A, a second electric conducting portion 63B, and a third electric conducting portion 63C. The first electric conducting portion 63A, the second electric conducting portion 63B, and the third electric conducting portion 63C extend along the longitudinal axis C. The first electric conducting portion 63A is electrically insulated from the second electric conducting portion 63B. The second electric conducting portion 63B is electrically insulated from the third electric conducting portion 63C. The first electric conducting portion 63A is electrically insulated from the third electric conducting portion 63C. When the vibrator case 11 is coupled to the movable cylindrical member 46 (sheath 5), a distal portion of the first electric conducting portion 63A alone is in electric contact with the first electric connection portion 62A of the electric connection ring 53. Similarly, a distal portion of the second electric conducting portion 63B alone is in electric contact with the second electric connection portion 62B of the electric connection ring 53. A distal portion of the third electric conducting portion 63C alone is in electric contact with the third electric connection portion 62C of the electric connection ring 53.

One end of an electric signal line 65 is connected to a proximal portion of the first electric conducting portion 63A. One end of an electric signal line 66 is connected to a proximal portion of the second electric conducting portion 63B. One end of an electric signal line 67 is connected to a proximal portion of the third electric conducting portion 63C. The other ends of the electric signal lines 65 to 67 are connected to the controller 10 of the power supply unit 7 through the inside of the cable 6.

As described above, a first electric signal path P1 is formed from the first switch portion 58A to the controller 10 of the power supply unit 7 through the electric signal line 61A, the first electric connection portion 62A, the first electric conducting portion 63A, and the electric signal line 65. A second electric signal path P2 is formed from the second switch portion 58B to the controller 10 of the power supply unit 7 through the electric signal line 61B, the second electric connection portion 62B, the second electric conducting portion 63B, and the electric signal line 66. Moreover, a ground path G is formed from the first switch portion 58A and the second switch portion 58B to the controller 10 through the electric signal line 61C, the third electric connection portion 62C, the third electric conducting portion 63C, and the electric signal line 67.

FIG. 7 is a circuit diagram showing an electric connection state between the first switch portion 58A, the second switch portion 58B, and the controller 10. As shown in FIG. 7, in the electric connection state described above, if the first treatment mode input button 57A is pressed, the first switch portion 58A is turned on (closed), and the first electric signal path P1 is electrically connected to the ground path G in the first switch portion 58A. As a result, an electric signal is transmitted to the controller 10 of the power supply unit 7 from the first treatment mode input button 57A (first switch portion 58A). An ultrasonic generating current is then output from the ultrasonic generating current supplier 8, and a high-frequency current is output from the high-frequency current supplier 9. That is, the first treatment mode is selected when the first treatment mode input button 57A is pressed.

If the second treatment mode input button 57B is pressed, the second switch portion 58B is turned on (closed), and the second electric signal path P2 is electrically connected to the ground path G in the second switch portion 58B. As a result, an electric signal is transmitted to the controller 10 of the power supply unit 7 from the second treatment mode input button 57B (second switch portion 58B). A high-frequency current is then output from the high-frequency current supplier 9. In this case, no ultrasonic generating current is output from the ultrasonic generating current supplier 8. That is, the second treatment mode, which is different from the first treatment mode, is selected when the second treatment mode input button 57B is pressed.

As shown in FIG. 6, the vibrator case 11 includes a fourth electric conducting portion 63D extending along the longitudinal axis C. The first electric conducting portion 63A, second electric conducting portion 63B, and third electric conducting portion 63C are all electrically insulated from the fourth electric conducting portion 63D. An electric signal line 69 extending from the high-frequency current supplier 9 of the power supply unit 7 through the inside of the cable 6 is connected to a proximal portion of the fourth electric conducting portion 63D. When the vibrator case 11 is coupled to the movable cylindrical member 46 (sheath 5), a distal portion of the fourth electric conducting portion 63D alone is in electric contact with the movable cylindrical member 46. In this way, a high-frequency current is transmitted between the high-frequency current supplier 9 and the movable cylindrical member 46 of the sheath 5 via the electric signal line 69 and the fourth electric conducting portion 63D.

As shown in FIG. 4, the sheath 5 includes a fixed cylindrical member 71 located to the inner peripheral direction side of the rotational operation knob 37. The fixed cylindrical member 71 is fixed to the rotational operation knob 37, and is made of an insulating material such as a resin. A proximal portion of an outer tube 72 and a proximal portion of an outer pipe 73 are fixed to a distal portion of the fixed cylindrical member 71. The outer tube 72 is located to an outer peripheral direction side of the outer pipe 73, and forms the exterior of the sheath 5. The outer tube 72 is made of an insulating material such as a resin. An inner tube 75 is provided to the inner peripheral direction side of the outer pipe 73. The inner tube 75 is made of an insulating material such as a resin, and is fixed to the outer pipe 73 via fixing pins 76A and 76B. The configuration described above allows the rotational operation knob 37 to be rotatable relative to the cylindrical case 31 together with the outer tube 72, the outer pipe 73, and the inner tube 75 in the directions around the longitudinal axis.

The sheath 5 includes an inner pipe 77 provided between the outer pipe 73 and the inner tube 75 in the diametrical directions. The inner pipe 77 is fixed to a distal portion of the movable cylindrical member 46 via a connection member 78 and a connection pin 79. The inner pipe 77 is movable relative to the outer tube 72, the outer pipe 73, and the inner tube 75 along the longitudinal axis C together with the movable cylindrical member 46. That is, the inner pipe 77 is movable relative to the handle unit 4 and the probe 3 along the longitudinal axis C together with the movable cylindrical member 46. Here, the movable cylindrical member 46 and the inner pipe 77 serve as a movable portion which is movable relative to the probe 3 along the longitudinal axis C.

As the inner pipe 77 is fixed to the movable cylindrical member 46, a rotational operation in the rotational operation knob 37 is transmitted via the movable cylindrical member 46. Therefore, the inner pipe 77 is rotatable relative to the cylindrical case 31 in the directions around the longitudinal axis together with the rotational operation knob 37. As described above, the rotational operation knob 37 is rotatable relative to the cylindrical case 31 in the directions around the longitudinal axis together with the outer tube 72, the outer pipe 73, and the inner tube 75. Thus, the sheath 5 is rotatable relative to the cylindrical case 31 in the directions around the longitudinal axis together with the rotational operation knob 37. The inner pipe 77 is made of an electrically conducting material such as a metal. A high-frequency current is transmitted between the movable cylindrical member 46 and the inner pipe 77 via the connection member 78 and the connection pin 79.

FIG. 8 is a diagram showing the distal portion of the probe 3, the distal portion of the sheath 5, and the jaw 42. As shown in FIG. 8, the outer tube 72, the outer pipe 73, the inner tube 75, and the inner pipe 77 extend to the distal portion of the sheath 5 along the longitudinal axis C. As shown in FIG. 3, support members 85 made of an insulating material are formed in the outer peripheral portion of a probe body 21. The support members 85 are arranged apart from one another in directions parallel to the longitudinal axis C. When the probe 3 is coupled to the horn 15, each of the support members 85 is located at the node position of the ultrasonic vibration.

The support members 85 support the probe between the probe 3 and the sheath 5. The support members 85 also prevent the contact between the inner tube 75 (sheath 5) and the probe 3. As described above, the connection cylindrical member 45 and the elastic member 51 are made of an insulating material, so that the probe 3 is electrically insulated from the movable cylindrical member 46 (sheath 5). Therefore, the sheath 5 is electrically insulated from the probe 3 by the connection cylindrical member 45, the elastic member 51, and the support members 85.

As shown in FIG. 8, the jaw 42 is attached to the distal portion of the sheath 5 (a distal portion of the outer tube 72 and a distal portion of the outer pipe 73) via a coupling pin 87. The jaw 42 is rotatable relative to the sheath 5 around the coupling pin 87. A distal portion of the inner pipe 77 is coupled to the jaw 42 via a connection pin 89. A high-frequency current is transmitted between the inner pipe 77 and the jaw 42 via the connection pin 89. As described above, a high-frequency current can be transmitted to the jaw 42 from the high-frequency current supplier 9 through the electric signal line 69, the fourth electric conducting portion 63D, the movable cylindrical member 46, and the inner pipe 77.

FIG. 9 is a diagram showing the configuration of the jaw 42. FIG. 10 is a sectional view taken along the line X-X in FIG. 8. As shown in FIG. 9 and FIG. 10, the jaw 42 includes a jaw body 91 attached to the sheath 5. The jaw body 91 is made of an electrically conducting material. A second electrode portion 93 is coupled to the jaw body 91 via a connection pin 92. The high-frequency current transmitted to the jaw 42 from the inner pipe 77 of the sheath 5 is transmitted to the second electrode portion 93 via the jaw body 91. When the high-frequency current is transmitted to the second electrode portion 93 through the sheath 5, the second electrode portion 93 has a second electric potential E2 different in intensity from the first electric potential E1.

A pad member 95, which is an insulating abutting member made of an insulating material, is attached to the second electrode portion 93. The pad member 95 includes a jaw perpendicularly facing surface (abutting portion) 97 which is perpendicular to the opening-and-closing directions of the jaw 42. Jaw obliquely facing surfaces 98A and 98B are formed by the second electrode portion 93 on both sides of the jaw perpendicularly facing surface 97 in width directions which are directions perpendicular to the longitudinal axis C and perpendicular to the opening-and-closing directions of the jaw 42. In a section perpendicular to the longitudinal axis C, the jaw obliquely facing surfaces 98A and 98B are oblique to the jaw perpendicularly facing surface 97.

As shown in FIG. 10, the first electrode portion 23 includes a probe perpendicularly facing surface 102 which is perpendicular to the opening-and-closing directions of the jaw 42. The probe perpendicularly facing surface 102 is parallel to the jaw perpendicularly facing surface 97, and faces the jaw perpendicularly facing surface 97. When the jaw 42 is closed relative to the first electrode portion 23 without a grasping target such as a blood vessel (living tissue) between the first electrode portion 23 and the jaw 42, the jaw perpendicularly facing surface 97 abuts on the probe perpendicularly facing surface 102 of the first electrode portion 23.

Probe obliquely facing surfaces 103A and 103B are formed by the first electrode portion 23 on both sides of the probe perpendicularly facing surface 102 in the width directions which are the directions perpendicular to the longitudinal axis C and perpendicular to the opening-and-closing directions of the jaw 42. The probe obliquely facing surface 103A is parallel to the jaw obliquely facing surface 98A, and the probe obliquely facing surface 103B is parallel to the jaw obliquely facing surface 98B. A clearance is always formed between the probe obliquely facing surface 103A and the jaw obliquely facing surface 98A and between the probe obliquely facing surface 103B and the jaw obliquely facing surface 98B when the jaw 42 is closed relative to the first electrode portion 23. That is, there is a clearance between the second electrode portion 93 and the first electrode portion 23 when the jaw perpendicularly facing surface 97 (pad member 95) is in abutment with the first electrode portion 23 (probe perpendicularly facing surface 102).

FIG. 11 is a sectional view taken along the line 11-11 in FIG. 4. As shown in FIG. 4 and FIG. 11, the first movable handle 33 and the second movable handle 35 are attached to the cylindrical case 31 via a support pin 111. The first movable handle 33 and the second movable handle 35 rotate relative to the cylindrical case 31 around the support pin 111. That is, the first movable handle 33 and the second movable handle 35 have the same rotation axis R0.

Figure 13A:
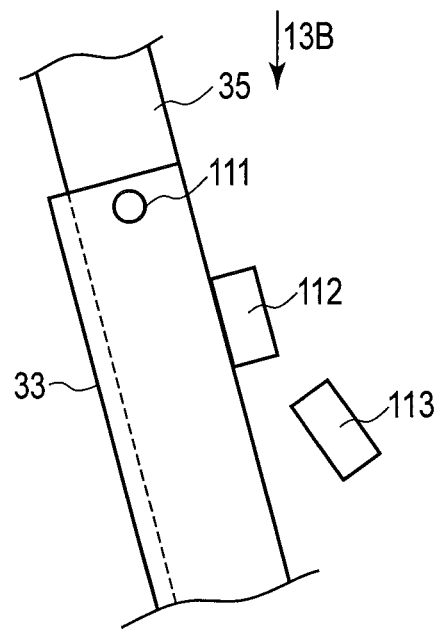
FIG. 13A is a schematic view showing a state in which a first movable handle according to the first embodiment is most-closed.
Figure 13B:
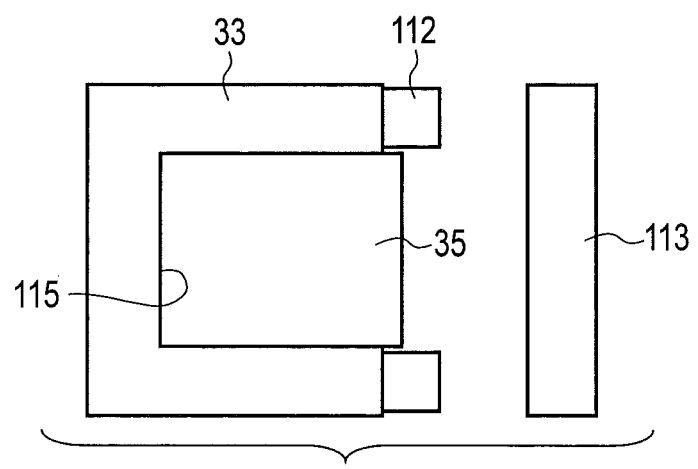
FIG. 13B is a schematic view of FIG. 13A seen from the direction of an arrow 13B.
Figure 13C:
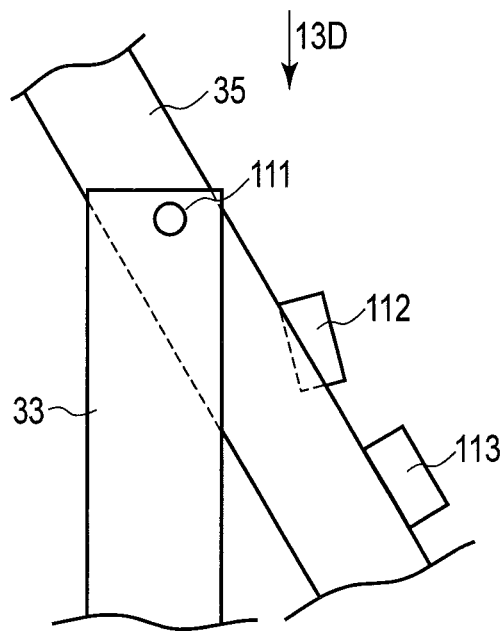
FIG. 13C is a schematic view showing a state in which a second movable handle according to the first embodiment is most-closed.
Figure 13D:
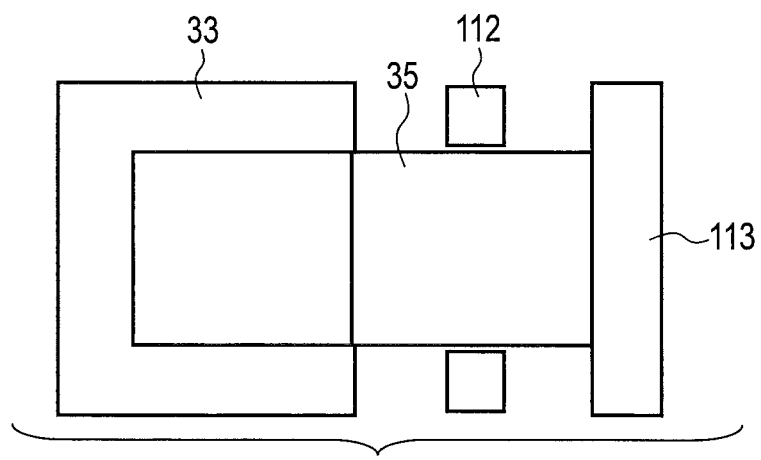
FIG. 13D is a schematic view of FIG. 13C seen from the direction of an arrow 13D.

FIG. 12A is a sectional view taken along the line 12A-12A in FIG. 4. FIG. 12B is a sectional view taken along the line 12B-12B in FIG. 4. FIG. 13A is a diagram showing a state in which the first movable handle 33 is most-closed. FIG. 13B is a view of FIG. 13A seen from a direction of an arrow 13B. FIG. 13C is a diagram showing a state in which the second movable handle 35 is most-closed. FIG. 13D is a view of FIG. 13C seen from a direction of an arrow 13D.

As shown in FIG. 4, FIG. 12A, and FIG. 12B, a first stopper portion 112 and a second stopper portion 113 are provide in the fixed handle 32. The first stopper portion 112 is located so that the first movable handle 33 can abut on the first stopper portion 112. As shown in FIG. 13A and FIG. 13B, the first movable handle 33 can be closed relative to the fixed handle 32 until the first movable handle 33 abuts on the first stopper portion 112. The second movable handle 35 does not abut on the first stopper portion 112. The second stopper portion 113 is located so that the second movable handle 35 can abut on the second stopper portion 113. As shown in FIG. 13C and FIG. 13D, the second movable handle 35 can be closed relative to the fixed handle 32 until the second movable handle 35 abuts on the second stopper portion 113. The first movable handle 33 does not abut on the second stopper portion 113.

As shown in FIG. 13A and FIG. 13B, the first movable handle 33 includes a press portion 115 which presses the second movable handle 35 toward the fixed handle 32 when the first movable handle 33 is closed relative to the fixed handle 32. When the first movable handle 33 is closed relative to the fixed handle 32, the second movable handle 35 is also closed together with the first movable handle 33. That is, when a surgeon (operator) operates the first movable handle 33 to close the jaw 42, the first movable handle 33 and the second movable handle 35 are closed together until the first movable handle 33 abuts on the first stopper portion 112. As shown in FIG. 13C and FIG. 13D, when the surgeon operates the second movable handle 35 to close the jaw 42, the first movable handle 33 is not closed. Therefore, when the second movable handle is operated to close the jaw 42, the second movable handle 35 is closed independently of the first movable handle 33 until the second movable handle 35 abuts on the second stopper portion 113.

As shown in FIG. 11, the second movable handle 35 includes arms 117A and 117B. The arm 117A is provided with an engaging protrusion 118A protruding toward the inner peripheral direction, and the arm 117B is provided with an engaging protrusion 118B protruding toward the inner peripheral direction.

As shown in FIG. 4 and FIG. 11, a slider portion 120 is provided to the outer peripheral direction side of the movable cylindrical member 46. In the slider portion 120, an engaging groove 121 which is depressed toward the inner peripheral direction is formed along the directions around the longitudinal axis. When the engaging protrusions 118A and 118B are engaged with the engaging groove 121, the second movable handle 35 is attached to the slider portion 120. The slider portion 120 is rotatable relative to the second movable handle 35 and the cylindrical case 31 in the directions around the longitudinal axis together with the movable cylindrical member 46 (sheath 5). The slider portion 120 is made of an insulating material. Therefore, the movable cylindrical member 46 (sheath 5) is electrically insulated from the second movable handle 35.

An elastic member unit 125 is provided to the outer peripheral direction side of the movable cylindrical member 46. The elastic member unit 125 includes a coil spring 126 which is an elastic member. The movable cylindrical member 46 (movable portion) is connected to the slider portion 120 by the coil spring 126. In a noncontact state in which the jaw 42 is out of contact with a grasping target, the coil spring 126 is attached between the movable cylindrical member 46 and the slider portion 120 in a reference state in which the coil spring 126 has contracted from the natural state by a contraction amount x0. Thus, in the noncontact state in which the jaw 42 is out of contact with the grasping target, elastic force k0x0 acts on the movable portion (the movable cylindrical member 46 and the inner pipe 77) from the coil spring 126 if the elastic coefficient of the coil spring 126 is k0. A stopper portion 127 is provided to the proximal direction side of the slider portion 120. The movement of the slider portion 120 toward the proximal direction is regulated by the stopper portion 127.

Figure 14A:
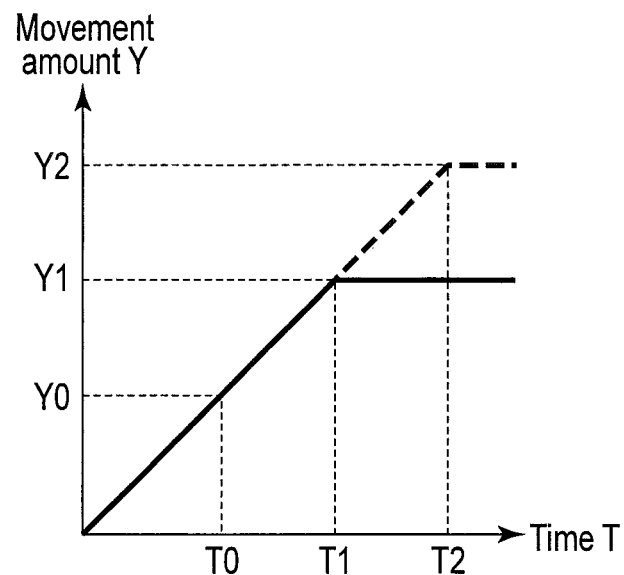
FIG. 14A is a schematic view showing a change with time in a movement amount of the first movable handle resulting from a close operation of the jaw according to the first embodiment in a first treatment mode, and a change with time in a movement amount of the second movable handle resulting from the close operation of the jaw according to the first embodiment in a second treatment mode.
Figure 14B:
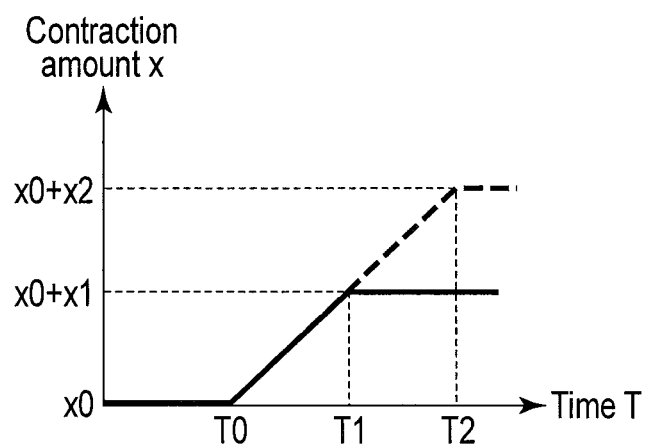
FIG. 14B is a schematic view showing a change with time in a contraction amount of a coil spring resulting from the close operation of the jaw according to the first embodiment in the first treatment mode, and a change with time in the contraction amount of the coil spring resulting from the close operation of the jaw according to the first embodiment in the second treatment mode.

Now, the functions of the grasping treatment device 1 according to the present embodiment are described. Here, FIG. 14A is a view showing a change with time in a movement amount of the first movable handle 33 resulting from a close operation of the jaw 42 in the first treatment mode, and a change with time in a movement amount of the second movable handle 35 resulting from the close operation of the jaw 42 in the second treatment mode. FIG. 14B is a view showing a change with time in a contraction amount of the coil spring 126 resulting from the close operation of the jaw 42 in the first treatment mode, and a change with time in the contraction amount of the coil spring 126 resulting from the close operation of the jaw 42 in the second treatment mode. In FIG. 14A and FIG. 14B, the change with time in the first treatment mode is indicated by a solid line, and the change with time in the second treatment mode is indicated by a broken line. In FIG. 14A and FIG. 14B, a time T is indicated on the horizontal axis. The time T indicates a time in which the first movable handle 33 or the second movable handle 35 is in the process of being closed.

When the grasping target is grasped between the first electrode portion 23 and the jaw 42 in the first treatment mode, the first movable handle 33 is operated to close the jaw 42, and the first movable handle 33 is closed relative to the fixed handle 32. At the same time, the second movable handle 35 is also closed together with the first movable handle 33. As a result, the first movable handle 33 and the second movable handle 35 rotate around the rotation axis R0, and the slider portion 120 and the movable portion (the movable cylindrical member 46 and the inner pipe 77) move toward the distal direction along the longitudinal axis C. In this case, as shown in FIG. 14A and FIG. 14B, the noncontact state in which the jaw 42 is out of contact with the grasping target is kept until a time T0 passes, so that the coil spring 126 does not contract from the reference state. Thus, the elastic force acting on the movable cylindrical member 46 and the inner pipe 77 from the coil spring 126 does not change from k0x0. The jaw 42 is closed relative to the first electrode portion 23 by the movement of the movable cylindrical member 46 and the inner pipe 77 toward the distal direction.

After the time T0 has passed, the jaw 42 comes into the contact state to contact a grasping target such as a living tissue. In this case, the first movable handle 33 has moved by a movement amount Y0. The closing of the jaw 42 is temporarily stopped by the contact of the jaw 42 with the grasping target. Therefore, the movement of the movable cylindrical member 46 and the inner pipe 77 toward the distal direction is temporarily stopped. When the first movable handle 33 and the second movable handle 35 are further closed relative to the fixed handle 32 in the contact state, the slider portion 120 moves relative to the movable cylindrical member 46 (movable portion) toward the distal direction.

The coil spring 126 further contracts from the reference state in response to the movement of the slider portion 120 relative to the movable cylindrical member 46. An elastic force acting on the movable cylindrical member 46 and the inner pipe 77 from the coil spring 126 when the coil spring 126 has further contracted from the reference state is k0(x0+x), wherein x is the contraction amount of the coil spring 126 from the reference state. This elastic force is greater than the elastic force k0x0 in the reference state. As the elastic force k0(x0+x) greater than the elastic force k0x0 in the reference state acts on the movable cylindrical member 46 (movable portion) from the coil spring 126, the movable cylindrical member 46 and the inner pipe 77 that have been temporarily stopped further move toward the distal direction. As a result, the jaw 42 which has come into contact with the grasping target is further closed relative to the first electrode portion 23. Therefore, a grasping force to grasp the grasping target between the jaw 42 and the first electrode portion 23 is greater than when the coil spring 126 is in the reference state.

As described above, in a contact state in which the jaw 42 is in contact with the grasping target, the slider portion 120 is moved relative to the movable portion (the movable cylindrical member 46 and the inner pipe 77) along the longitudinal axis C by the open-or-close operation in the first movable handle 33. As a result, the contraction amount of the coil spring 126 which is an elastic member changes, and the elastic force acting on the movable cylindrical member 46 (movable portion) from the coil spring 126 changes by the change of the contraction amount of the coil spring 126. Therefore, the elastic force between the first electrode portion 23 and the jaw 42 is changed by the elastic member unit 125.

After a time T1 has passed, the first movable handle 33 moves in a movement amount Y1. The first movable handle 33 which has moved in the movement amount Y1 abuts on the first stopper portion 112, and the closing of the first movable handle 33 and the second movable handle 35 is stopped. In this case, the coil spring 126 has contracted by a first contraction amount x1 from the reference state. Thus, first elastic force k0(x0+x1) acts on the movable portion (the movable cylindrical member 46 and the inner pipe 77) from the coil spring 126 (elastic member unit 125). As a result, the grasping target is grasped between the first electrode portion 23 and the jaw 42 with first grasping force F1.

In the first treatment mode, the surgeon presses the first treatment mode input button 57A, which is the first treatment mode input portion, when the grasping target is grasped between the first electrode portion 23 and the jaw 42 with the first grasping force F1. As a result, the first switch portion 58A is turned on, the first electric signal path P1 is electrically connected to the ground path G in the first switch portion 58A, and an electric signal is transmitted to the controller 10 of the power supply unit 7 from the first treatment mode input button 57A (first switch portion 58A). An ultrasonic generating current is then output from the ultrasonic generating current supplier 8, and a high-frequency current is output from the high-frequency current supplier 9.

The ultrasonic vibration is generated in the ultrasonic vibrator 12 by the supply of a current to the ultrasonic vibrator 12 from the ultrasonic generating current supplier 8 via the electric signal lines 13A and 13B. The ultrasonic vibration is then transmitted to the first electrode portion 23. The grasping target grasped between the first electrode portion 23 and the jaw 42 is cut and coagulated by frictional heat generated by the ultrasonic vibration of the probe 3.

The high-frequency current output from the high-frequency current supplier 9 is transmitted to the first electrode portion 23 through the electric signal line 17, the ultrasonic vibrator 12, the horn 15, and the probe 3. When the high-frequency current is transmitted to the first electrode portion 23, the first electrode portion 23 has the first electric potential E1. A high-frequency current is also transmitted to the second electrode portion 93 from the high-frequency current supplier 9 through the electric signal line 69, the fourth electric conducting portion 63D, the movable cylindrical member 46, the inner pipe 77, and the jaw 42. When the high-frequency current is transmitted to the second electrode portion 93, the second electrode portion 93 has the second electric potential E2, which is different in intensity (mass) from the first electric potential E1. The first electrode portion 23 has the first electric potential E1, and the second electrode portion 93 has the second electric potential E2, so that a high-frequency current runs through the grasping target grasped between the first electrode portion 23 and the jaw 42. Consequently, a grasping target such as a living tissue is reformed, and the coagulation is accelerated.

In the first treatment mode, the first movable handle 33 and the second movable handle 35 are opened relative to the fixed handle 32 by the operation of the first movable handle 33 to open the jaw 42 from the condition in which the grasping target is grasped between the jaw 42 and the first electrode portion 23. At the same time, the slider portion 120 moves relative to the movable cylindrical member 46 (movable portion) toward the proximal direction. As a result, the coil spring 126 is stretched into the reference state. The slider portion 120 and the movable portion (the movable cylindrical member 46 and the inner pipe 77) then move together toward the proximal direction along the longitudinal axis C. The jaw 42 is opened relative to the first electrode portion 23 by the movement of the movable cylindrical member 46 and the inner pipe 77 toward the proximal direction.

When the grasping target is grasped between the first electrode portion 23 and the jaw 42 in the second treatment mode, the second movable handle 35 is operated to close the jaw 42, and the second movable handle 35 is closed relative to the fixed handle 32. In this case, the first movable handle 33 is not closed, and the second movable handle 35 is closed independently of the first movable handle 33. As a result, the second movable handle 35 rotates around the rotation axis R0, and the slider portion 120 and the movable portion (the movable cylindrical member 46 and the inner pipe 77) move together toward the distal direction along the longitudinal axis C.

In this case, as shown in FIG. 14A and FIG. 14B, the change with time in the movement amount of the second movable handle 35 is similar to the change of the first movable handle 33 with time in the first treatment mode until the time T1 passes. Therefore, the change with time in the contraction amount of the coil spring 126 is similar to that in the first treatment mode until the time T1 passes. That is, in the contact state in which the jaw 42 is in contact with the grasping target, the slider portion 120 is moved relative to the movable portion (the movable cylindrical member 46 and the inner pipe 77) along the longitudinal axis C by the open-or-close operation in the second movable handle 35. As a result, the contraction amount of the coil spring 126 which is an elastic member changes, and the elastic force acting on the movable cylindrical member 46 (movable portion) from the coil spring 126 changes in accordance with the change of the contraction amount of the coil spring 126. Therefore, the elastic force between the first electrode portion 23 and the jaw 42 is changed by the elastic member unit 125.

However, when the second movable handle 35 is operated to close the jaw 42, the second movable handle 35 is further closed from the condition in which the second movable handle 35 has moved in the movement amount Y1 even after the passage of the time T1. Thus, the coil spring 126 further contracts from the condition in which the coil spring 126 has contracted in the first contraction amount x1 from the reference state.

After a time T2 longer than the time T1 has passed, the second movable handle 35 moves by a movement amount Y2. Having moved by the movement amount Y2, the second movable handle 35 abuts on the second stopper portion 113, and the closing of the second movable handle 35 is stopped. In this case, the coil spring 126 has contracted by a second contraction amount x2 greater than the first contraction amount x1 from the reference state. Thus, second elastic force k0(x0+x2) greater than—the first elastic force k0(x0+x1) acts on the movable portion (the movable cylindrical member 46 and the inner pipe 77) from the coil spring 126 (elastic member unit 125). In the second treatment mode, the second elastic force k0(x0+x2) greater than the first elastic force k0(x0+x1) acts on the movable portion, so that the grasping target is grasped while the jaw 42 is further closed relative to the first electrode portion 23 than in the first treatment mode. Therefore, in the second treatment mode, the grasping target is grasped between the first electrode portion 23 and the jaw 42 with second grasping force F2 greater than the first grasping force F1.

In the second treatment mode, the surgeon presses the second treatment mode input button 57B, which is the second treatment mode input portion, when the grasping target is grasped between the first electrode portion 23 and the jaw 42 with the second grasping force F2. As a result, the second switch portion 58B is turned on, the second electric signal path P2 is electrically connected to the ground path G in the second switch portion 58B, and an electric signal is transmitted to the controller 10 of the power supply unit 7 from the second switch portion 58B. A high-frequency current is then output from the high-frequency current supplier 9. In this case, no current is output from the ultrasonic generating current supplier 8.

The high-frequency current output from the high-frequency current supplier 9 is transmitted to the first electrode portion 23 through the electric signal line 17, the ultrasonic vibrator 12, the horn 15, and the probe 3. When the high-frequency current is transmitted to the first electrode portion 23, the first electrode portion 23 has the first electric potential E1. A high-frequency current is also transmitted to the second electrode portion 93 from the high-frequency current supplier 9 through the electric signal line 69, the fourth electric conducting portion 63D, the movable cylindrical member 46, the inner pipe 77, and the jaw 42. When the high-frequency current is transmitted to the second electrode portion 93, the second electrode portion 93 has the second electric potential E2 different in intensity from the first electric potential E1. In the second treatment mode, the high-frequency current alone is transmitted to the first electrode portion 23 and the second electrode portion 93. The first electrode portion 23 has the first electric potential E1, and the second electrode portion 93 has the second electric potential E2, so that a high-frequency current runs through the grasping target grasped between the first electrode portion 23 and the jaw 42. Consequently, a grasping target such as a living tissue is reformed and coagulated.

In the second treatment mode, the grasping target is grasped between the first electrode portion 23 and the jaw 42 with the second grasping force F2 greater than the first grasping force F1 in the first treatment mode. Thus, the reformation of the living tissue (grasping target) with the high-frequency current is more accelerated in the second treatment mode than in the first treatment mode. Therefore, the performance of the coagulation of the grasping target with the high-frequency current is improved, so that the deterioration in the performance of the coagulation of the grasping target is prevented in the second treatment mode, which does not use the ultrasonic vibration. Consequently, the grasping target (living tissue) is stably sealed in the second treatment mode, which does not use the ultrasonic vibration.

As described above, in the present embodiment, the fixed handle 32, the first movable handle 33, and the second movable handle 35 serve as a contraction amount converter configured to convert a contraction amount so that the second contraction amount x2 of the coil spring (elastic member) 126 in the second treatment mode is greater than the first contraction amount x1 of the coil spring (elastic member) 126 in the first treatment mode. Thus, the fixed handle 32, the first movable handle 33, and the second movable handle 35 serve as an elastic force converter configured to convert an elastic force so that the second elastic force k0(x0+x2) acting on the movable portion (the movable cylindrical member 46 and the inner pipe 77) from the elastic member unit 125 in the second treatment mode is greater than the first elastic force k0(x0+x1) acting on the movable portion (46 and 77) from the elastic member unit 125 in the first treatment mode. Therefore, the fixed handle 32, the first movable handle 33, and the second movable handle 35 serve as a grasping force converting unit configured to convert a grasping force so that the second grasping force F2 between the first electrode portion 23 and the jaw 42 in the second treatment mode is greater than the first grasping force F1 between the first electrode portion 23 and the jaw 42 in the first treatment mode.

Accordingly, the grasping treatment device 1 having the configuration described above provides the following advantageous effects. In the grasping treatment device 1, the second contraction amount x2 of the coil spring (elastic member) 126 in the second treatment mode is greater than the first contraction amount x1 of the coil spring (elastic member) 126 in the first treatment mode. Thus, the second elastic force k0(x0+x2) acting on the movable portion (the movable cylindrical member 46 and the inner pipe 77) from the elastic member unit 125 in the second treatment mode is greater than the first elastic force k0(x0+x1) acting on the movable portion (46 and 77) from the elastic member unit 125 in the first treatment mode. Therefore, in the second treatment mode, the grasping target is grasped between the first electrode portion 23 and the jaw 42 with the second grasping force F2 greater than the first grasping force F1 in the first treatment mode. Thus, the reformation of the living tissue (grasping target) with the high-frequency current is more accelerated in the second treatment mode than in the first treatment mode. Therefore, the performance of the coagulation of the grasping target with the high-frequency current is improved, so that deterioration in the performance of the coagulation of the grasping target can be prevented in the second treatment mode, which does not use the ultrasonic vibration. Consequently, the grasping target (living tissue) can be stably sealed in the second treatment mode, which does not use the ultrasonic vibration.

Modification of First Embodiment

Figure 15:
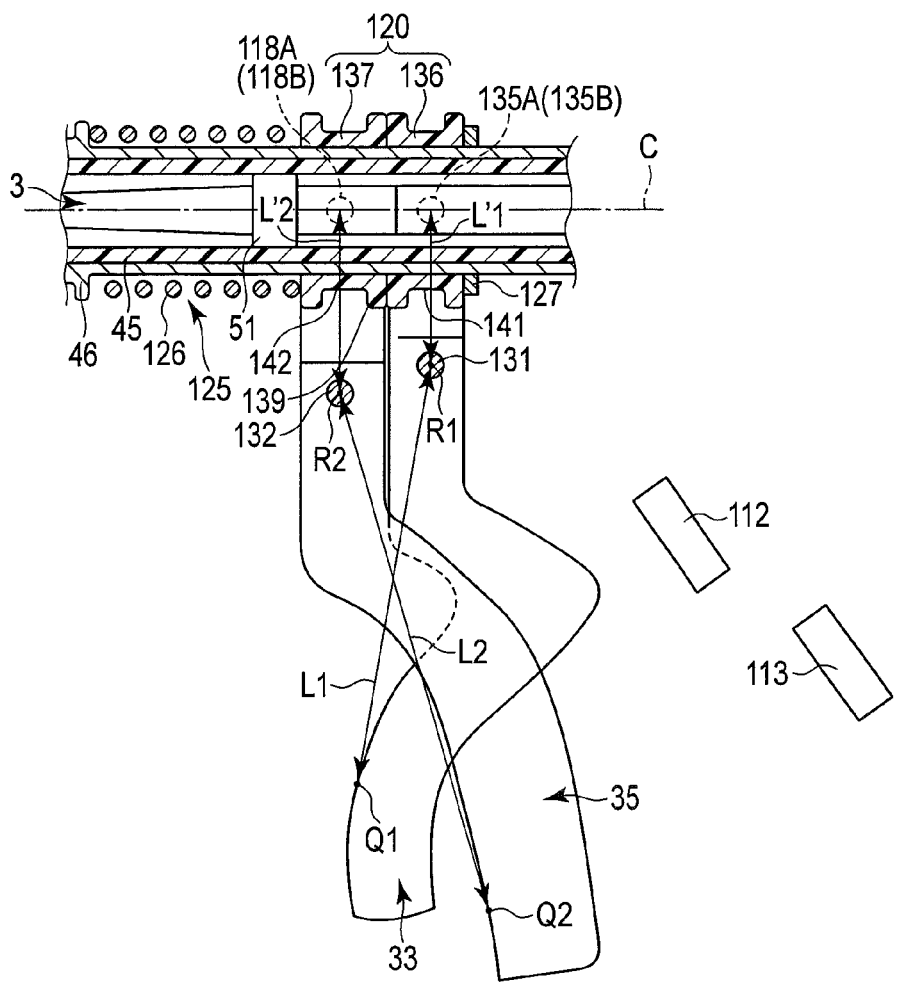
FIG. 15 is a schematic sectional view showing a coupling configuration between the handle unit and the sheath according to a modification of the first embodiment.
Figure 16:
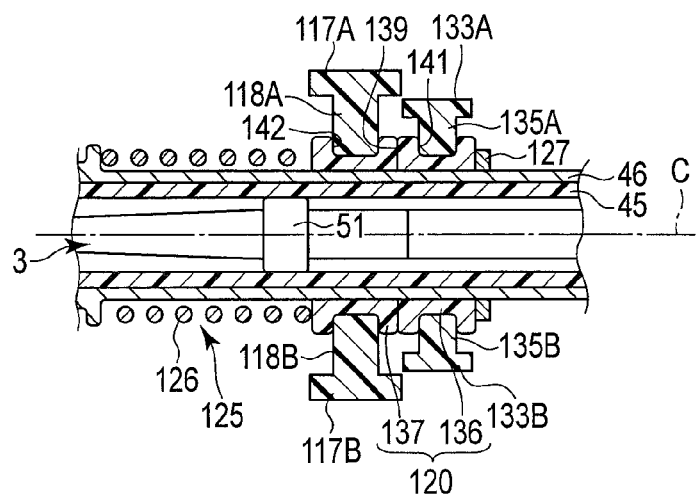
FIG. 16 is a schematic sectional view showing, in a section different from that in FIG. 15, the coupling configuration between the handle unit and the sheath according to the modification of the first embodiment.

While the first movable handle 33 and the second movable handle 35 have the same rotation axis R0 in the first embodiment, the present invention is not limited to this. For example, as in a modification shown in FIG. 15 and FIG. 16, the first movable handle 33 may be attached to the cylindrical case 31 via a support pin 131, and the second movable handle 35 may be attached to the cylindrical case 31 via a support pin 132. In this case, the first movable handle 33 has a first rotation axis R1, and the second movable handle 35 has a second rotation axis R2 different from the first rotation axis R1. As in the first embodiment, the second movable handle 35 has the engaging protrusions 118A and 118B. In the present modification, arms 133A and 133B are provided in the first movable handle 33. The arm 133A is provided with an engaging protrusion 135A protruding toward the inner peripheral direction, and the arm 133B is provided with an engaging protrusion 135B protruding toward the inner peripheral direction. In the present modification, the slider portion 120 includes a first slider 136, and a second slider 137 provided to the distal direction side of the first slider 136. In the first slider 136, an engaging groove 141 which is depressed toward the inner peripheral direction is formed along the directions around the longitudinal axis. In the second slider 137, an engaging groove 142 which is depressed toward the inner peripheral direction is formed along the directions around the longitudinal axis. When the engaging protrusions 135A and 135B are engaged with the engaging groove 141, the first movable handle 33 is attached to the first slider 136 (slider portion 120). When the engaging protrusions 118A and 118B are engaged with the engaging groove 142, the second movable handle 35 is attached to the second slider 137 (slider portion 120).

The first slider 136 and the second slider 137 are rotatable together with the movable cylindrical member 46 (sheath 5) relative to the first movable handle 33, the second movable handle 35, and the cylindrical case 31 in the directions around the longitudinal axis. The first slider 136 and the second slider 137 are made of an insulating material. Therefore, the movable cylindrical member 46 (sheath 5) is electrically insulated from the first movable handle 33 and the second movable handle 35.

One end of the coil spring 126 of the elastic member unit 125 is connected to the second slider 137. The first slider 136 is provided with a press portion 139 which presses the second slider 137 in the distal direction when the first slider 136 moves relative to the movable cylindrical member 46 toward the distal direction.

When the grasping target is grasped between the first electrode portion 23 and the jaw 42 in the first treatment mode, the first movable handle 33 is operated to close the jaw 42, and the first movable handle 33 is closed relative to the fixed handle 32. At the same time, the press portion 139 of the first slider 136 presses the second slider 137 toward the distal direction, and the second movable handle 35 thereby moves in the same direction as the first movable handle 33. After the time T0 has passed, the jaw 42 comes into the contact state to contact the grasping target, and the first slider 136 moves relative to the movable cylindrical member 46. At the same time, the press portion 139 of the first slider 136 presses the second slider 137 toward the distal direction, and the second slider 137 thereby moves relative to the movable cylindrical member 46 (movable portion) together with the first slider 136. In response to the movement of the second slider 137, the coil spring 126 contracts from the reference state.

As in the first embodiment, the first movable handle 33 moves in the movement amount Y1 after the time T1 has passed. The first movable handle 33 which has moved in the movement amount Y1 abuts on the first stopper portion 112, and the closing of the first movable handle 33 is stopped. In this case, the coil spring 126 has contracted by the first contraction amount x1 from the reference state. Thus, the first elastic force k0(x0+x1) acts on the movable portion (the movable cylindrical member 46 and the inner pipe 77) from the coil spring 126 (elastic member unit 125). As a result, the grasping target is grasped between the first electrode portion 23 and the jaw 42 with the first grasping force F1.

When the grasping target is grasped between the first electrode portion 23 and the jaw 42 in the second treatment mode, the second movable handle 35 is operated to close the jaw 42, and the second movable handle 35 is closed relative to the fixed handle 32. In this case, the first movable handle 33 is not closed. After the time T0 has passed, the jaw 42 comes into the contact state to contact the grasping target, and the second slider 137 moves relative to the movable cylindrical member 46 independently of the first slider 136. As a result, the coil spring 126 contracts from the reference state. In this case, the first slider 136 does not move.

As in the first embodiment, after the time T2 longer than the time T1 has passed, the second movable handle 35 moves in the movement amount Y2 greater than the movement amount Y1. Having moved in the movement amount Y2, the second movable handle 35 abuts on the second stopper portion 113, and the closing of the second movable handle 35 is stopped. In this case, the coil spring 126 has contracted in the second contraction amount x2 greater than the first contraction amount x1 from the reference state. Thus, second elastic force k0(x0+x2) greater than the first elastic force k0(x0+x1) acts on the movable portion (the movable cylindrical member 46 and the inner pipe 77) from the coil spring 126 (elastic member unit 125). In the second treatment mode, the second elastic force k0(x0+x2) greater than the first elastic force k0(x0+x1) acts on the movable portion, so that the grasping target is grasped while the jaw 42 is further closed relative to the first electrode portion 23 than in the first treatment mode. Therefore, in the second treatment mode, the grasping target is grasped between the first electrode portion 23 and the jaw 42 with the second grasping force F2 greater than the first grasping force F1.

As described above, in the present modification as well, the fixed handle 32, the first movable handle 33, and the second movable handle 35 serve as a contraction amount converter configured to convert a contraction amount so that the second contraction amount x2 of the coil spring (elastic member) 126 in the second treatment mode is greater than the first contraction amount x1 of the coil spring (elastic member) 126 in the first treatment mode, as in the first embodiment. Thus, the fixed handle 32, the first movable handle 33, and the second movable handle 35 serve as an elastic force converter configured to convert an elastic force so that the second elastic force k0(x0+x2) acting on the movable portion (the movable cylindrical member 46 and the inner pipe 77) from the elastic member unit 125 in the second treatment mode is greater than the first elastic force k0(x0+x1) acting on the movable portion (46 and 77) from the elastic member unit 125 in the first treatment mode. Therefore, the fixed handle 32, the first movable handle 33, and the second movable handle 35 serve as a grasping force converting unit configured to convert a grasping force so that the second grasping force F2 between the first electrode portion 23 and the jaw 42 in the second treatment mode is greater than the first grasping force F1 between the first electrode portion 23 and the jaw 42 in the first treatment mode.

In the present modification, the leverage of the first movable handle 33 is L1/L'1, wherein L1 is a dimension between a first force application point Q1 of the first movable handle 33 where force is applied from the surgeon in the open-or-close operation of the jaw 42 in the first treatment mode and the first rotation axis R1 which is a supporting point of the first movable handle 33, and L'1 is a dimension between the first rotation axis R1 and the engaging protrusions 135A and 135B which are action points. The leverage of the second movable handle 35 is L2/L'2, wherein L2 is a dimension between a second force application point Q2 of the second movable handle 35 where force is applied from the surgeon in the open-or-close operation of the jaw 42 in the second treatment mode and the second rotation axis R2 which is a supporting point of the second movable handle 35, and L'2 is a dimension between the second rotation axis R2 and the engaging protrusions 118A and 118B which are action points.

Here, in the first embodiment, the supporting point of the second movable handle 35 is the rotation axis R0, and the action points of the second movable handle 35 are the engaging protrusions 118A and 118B, both in the first treatment mode and the second treatment mode. The force application point where force is applied from the surgeon in the open-or-close operation of the jaw 42 in the first treatment mode is different from that in the second treatment mode. Therefore, in the first embodiment, the leverage of the second movable handle 35 in the first treatment mode is different from that in the second treatment mode. Thus, even when the surgeon performs the open-or-close operation by the application of the same magnitude of force in the first treatment mode and the second treatment mode, the movement amount of the slider portion 120 in the first treatment mode is different from that in the second treatment mode. Therefore, the ratio of the contraction amount of the coil spring 126 responsive to the force applied by the surgeon in the open-or-close operation varies between the first treatment mode and the second treatment mode. Thus, the operability in the open-or-close operation of the jaw 42 may deteriorate.

In contrast, in the present modification, the leverage L1/L'1 of the first movable handle 33 and the leverage L2/L'2 of the second movable handle 35 can be adjusted by the adjustment of the dimensions L1, L2, L'1, and L'2. Thus, the grasping force between the jaw 42 and the first electrode portion 23 can be increased without the application of great force to the second movable handle 35. That is, the operability of the jaw is ensured by the adjustment of the leverage in the second treatment mode, which also has a large grasping force.

Second Embodiment

Now, a second embodiment of the present invention is described with reference to FIG. 17 to FIG. 21. In the second embodiment, the configuration according to the first embodiment is modified as below. The same parts as those in the first embodiment are provided with the same reference signs, and are not described.

Figure 17:
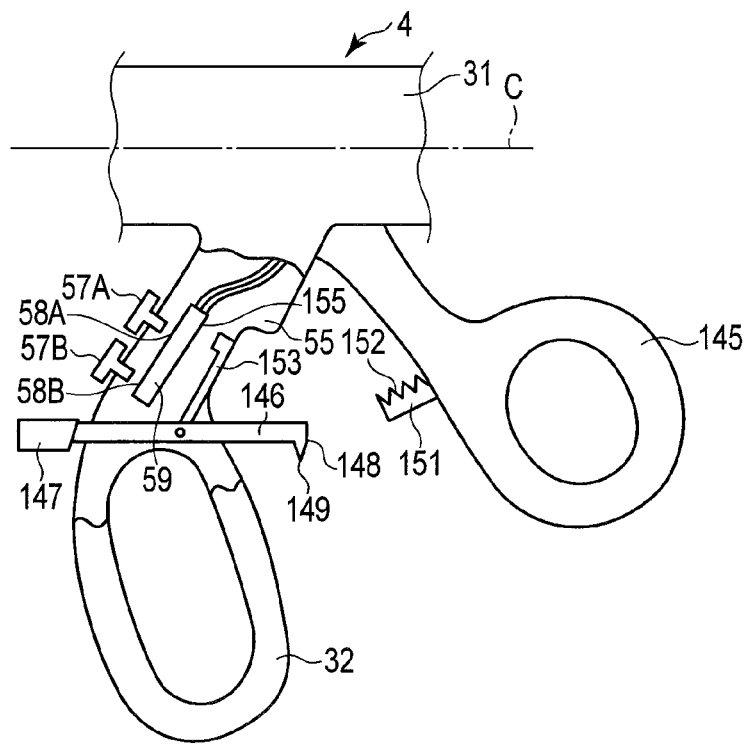
FIG. 17 is a schematic view showing the configuration of a handle unit of a grasping treatment device according to a second embodiment of the present invention in the first treatment mode.
Figure 18:
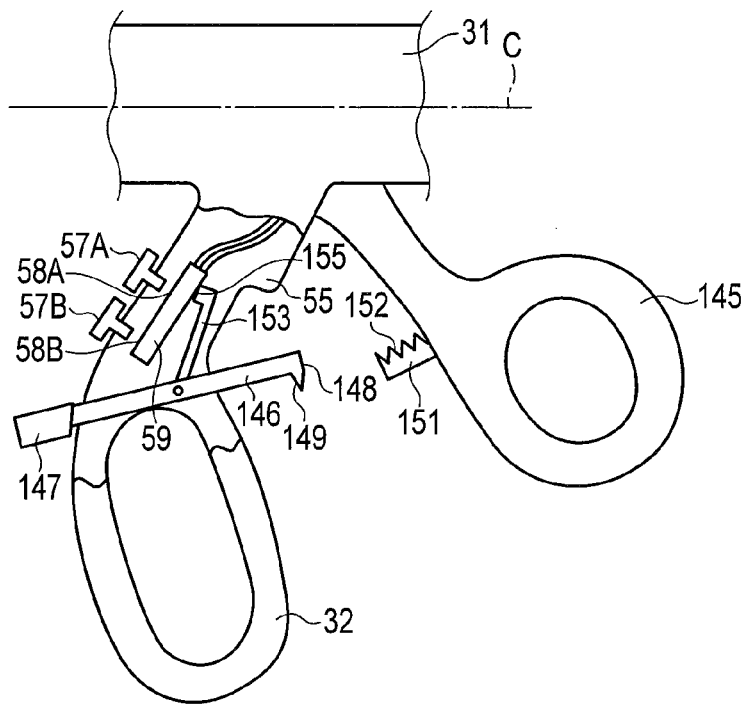
FIG. 18 is a schematic view showing the configuration of the handle unit of the grasping treatment device according to the second embodiment in the second treatment mode.

FIG. 17 and FIG. 18 are diagrams showing the configuration of a handle unit 4 of a grasping treatment device 1 according to the present embodiment. FIG. 17 shows a first treatment mode. FIG. 18 shows a second treatment mode. As shown in FIG. 17 and FIG. 18, the handle unit 4 according to the present embodiment includes a cylindrical case 31, a fixed handle 32, and a switch arrangement portion 55, as in the first embodiment. However, in the present embodiment, only one movable handle 145 configured to open or close relative to the fixed handle 32 is provided. The movable handle 145 is located to the proximal direction side of the fixed handle 32. In the present modification as well, the movable handle 145 is configured to open or close relative to the fixed handle 32 substantially parallel with the longitudinal axis C, as in the first embodiment. The movable handle 145 is attached to a slider portion 120 in the same manner as the second movable handle 35 according to the first embodiment.

A movement member 146 is attached to the fixed handle 32. The movement member 146 is movable between a first movement position (see FIG. 17) and a second movement position (see FIG. 18). The movement member 146 is moved by a changeover operation in a member position changeover lever 147 which is a member position changeover portion. The movement member 146 includes a stopper portion 148 and a fixed side ratchet 149. The movable handle 145 is provided with a protruding portion 151 protruding toward the fixed handle 32. A movable side ratchet 152 is formed in the protruding portion 151.

In the first treatment mode, the movement member 146 is moved to the first movement position by the changeover operation in the member position changeover lever 147. When a grasping target is grasped between a first electrode portion 23 and a jaw 42, the movable handle 145 is operated to close the jaw 42, and the movable handle 145 is closed relative to the fixed handle 32. In response to the close operation of the movable handle 145, a movable portion (a movable cylindrical member 46 and an inner pipe 77) of a sheath 5 moves relative to the handle unit 4 and a probe 3 toward the distal direction along a longitudinal axis C. The jaw 42 is closed relative to the first electrode portion 23 by the movement of the inner pipe 77. As in the first embodiment, after the time T0 has passed, the jaw 42 comes into the contact state to contact the grasping target, and the slider portion 120 moves relative to the movable cylindrical member 46. A coil spring 126 contracts from the reference state by the movement of the slider portion 120.

As in the first embodiment, after the time T1 has passed, the movable handle 145 moves in the movement amount Y1. When the mobile member 146 is located at the first movement position, the protruding portion 151 of the movable handle 145 abuts on the stopper portion 148 of the movement member 146 as a result of the movement the movable handle 145 in the movement amount Y1. Thereby, the close operation of the movable handle 145 is stopped. In this case, the coil spring 126 has contracted in the first contraction amount x1 from the reference state. Thus, the first elastic force k0(x0+x1) acts on the movable portion (the movable cylindrical member 46 and the inner pipe 77) from the coil spring 126 (elastic member unit 125). As a result, the grasping target is grasped between the first electrode portion 23 and the jaw 42 with the first grasping force F1.

In the second treatment mode, the movement member 146 is moved to the second movement position by the changeover operation in the member position changeover lever 147. When the grasping target is grasped between the first electrode portion 23 and the jaw 42, the movable handle 145 is operated to close the jaw 42, and the movable handle 145 is closed relative to the fixed handle 32, as in the first treatment mode. After the time T0 has passed, the jaw 42 comes into the contact state to contact the grasping target, and the slider portion 120 moves relative to the movable cylindrical member 46. As a result, the coil spring 126 contracts from the reference state.

When the movement member 146 is located at the second movement position, the protruding portion 151 of the movable handle 145 does not abut on the stopper portion 148 of the movement member 146 even if the movement the movable handle 145 moves by the movement amount Y1. Moreover, when the mobile member 146 is located at the second movement position, the movable side ratchet 152 of the protruding portion 151 is toothed with the fixed side ratchet 149 of the movement member 146. In the second treatment mode, the movable handle 145 is closed while the movable side ratchet 152 is toothed with the fixed side ratchet 149. That is, the fixed side ratchet 149 serves as a guide portion which guides the close motion of the movable handle 145 in the second treatment mode.

When the close motion of the movable handle 145 is guided by the fixed side ratchet 149, the movable handle 145 moves by the movement amount Y2 greater than the movement amount Y1 after the time T2 longer than the time T1 has passed, as in the first embodiment. In this case, the coil spring 126 has contracted by the second contraction amount x2 greater than the first contraction amount x1 from the reference state. Thus, the second elastic force k0(x0+x2) greater than the first elastic force k0(x0+x1) acts on the movable portion (the movable cylindrical member 46 and the inner pipe 77) from the coil spring 126 (elastic member unit 125). In the second treatment mode, the second elastic force k0(x0+x2) greater than the first elastic force k0(x0+x1) acts on the movable portion, so that the grasping target is grasped while the jaw 42 is further closed relative to the first electrode portion 23 than in the first treatment mode. Therefore, in the second treatment mode, the grasping target is grasped between the first electrode portion 23 and the jaw 42 with the second grasping force F2 greater than the first grasping force F1.

As described above, in the present embodiment, the member position changeover lever 147 serves as a contraction amount converter configured to convert a contraction amount so that the second contraction amount x2 of the coil spring (elastic member) 126 in the second treatment mode is greater than the first contraction amount x1 of the coil spring (elastic member) 126 in the first treatment mode. Thus, the member position changeover lever 147 serves as an elastic force converter configured to convert an elastic force so that the second elastic force k0(x0+x2) acting on the movable portion (the movable cylindrical member 46 and the inner pipe 77) from the elastic member unit 125 in the second treatment mode is greater than the first elastic force k0(x0+x1) acting on the movable portion (46 and 77) from the elastic member unit 125 in the first treatment mode. Therefore, the member position changeover lever 147 serves as a grasping force converting unit configured to convert a grasping force so that the second grasping force F2 between the first electrode portion 23 and the jaw 42 in the second treatment mode is greater than the first grasping force F1 between the first electrode portion 23 and the jaw 42 in the first treatment mode.

As shown in FIG. 17 and FIG. 18, a columnar insulating member 153 is attached to the movement member 146. The insulating member 153 is moved together with the movement member 146 by the changeover operation in the member position changeover lever 147. When the movement member 146 is located at the first movement position, the insulating member 153 is located apart from an electric circuit substrate 59 (see FIG. 17). When the movement member 146 is located at the second movement position, the insulating member 153 is in contact with the electric circuit substrate 59 (see FIG. 18).

Figure 19:
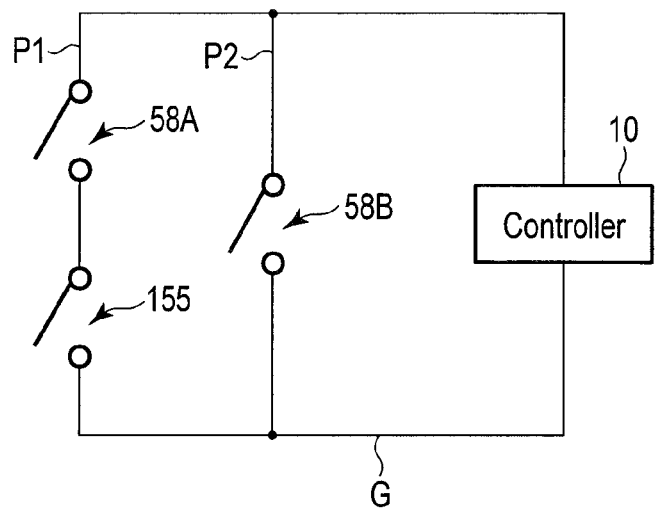
FIG. 19 is a circuit diagram showing an electric connection state between a first switch portion, a second switch portion, and a controller according to the second embodiment.

FIG. 19 is a circuit diagram showing an electric connection state between a first switch portion 58A, a second switch portion 58B, and a controller 10 according to the present embodiment. As shown in FIG. 19, in the present embodiment, a third switch portion 155 is provided in a first electric signal path P1 in addition to the first switch portion 58A and the second switch portion 58B. The third switch portion 155 is located on the electric circuit substrate 59.

Figure 20:
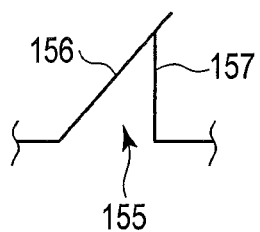
FIG. 20 is a schematic view showing the configuration of a third switch portion according to the second embodiment in the first treatment mode.
Figure 21:
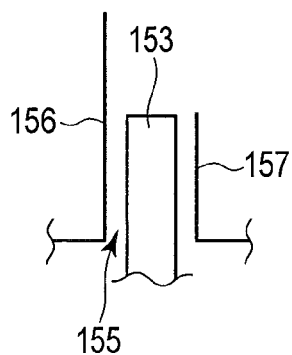
FIG. 21 is a schematic view showing the configuration of the third switch portion according to the second embodiment in the second treatment mode.

FIG. 20 and FIG. 21 are diagrams showing the configuration of the third switch portion 155. FIG. 20 shows the first treatment mode. FIG. 21 shows the second treatment mode. As shown in FIG. 20 and FIG. 21, the third switch portion 155 includes a first electric contact 156 and a second electric contact 157. The first electric contact 156 and the second electric contact 157 are urged into contact with each other.

As shown in FIG. 20, the insulating member 153 is located apart from an electric circuit substrate 59 in the first treatment mode. Thus, the first electric contact 156 and the second electric contact 157 are urged into contact with each other. Therefore, the third switch portion 155 is turned on (closed).

Thus, the first switch portion 58A is turned on (closed) when the surgeon presses a first treatment mode input button 57A which is a first treatment mode input portion. As a result, the first electric signal path P1 is electrically connected to a ground path G in the first switch portion 58A, and an electric signal is transmitted to the controller 10 of the power supply unit 7 from the first treatment mode input button 57A (first switch portion 58A).

As shown in FIG. 21, the insulating member 153 is in contact with the electric circuit substrate 59 in the second treatment mode. Thus, the insulating member 153 is inserted between the first electric contact 156 and the second electric contact 157, and the first electric contact 156 is insulated from the second electric contact 157. Therefore, the third switch portion 155 is turned off (opened), and the first treatment mode input button 57A (first switch portion 58A) is electrically disconnected from the controller 10 of the power supply unit 7. Thus, even when the surgeon presses the first treatment mode input button 57A which is the first treatment mode input portion and the first switch portion 58A is turned on (closed), the electric signal is not transmitted to the controller 10 of the power supply unit 7 from the first treatment mode input button 57A (first switch portion 58A). Therefore, even if the surgeon erroneously presses the first treatment mode input button 57A in a treatment in the second treatment mode, no ultrasonic generating current is output from an ultrasonic generating current supplier 8. As described above, in the second treatment mode, the third switch portion 155 is turned off by the insulating member 153. That is, the insulating member 153 serves as an electric disconnection portion which electrically disconnects the first treatment mode input button 57A from the controller 10 so that the electric signal is not transmitted to the controller 10 from the first treatment mode input button 57A in the second treatment mode regardless of whether the input operation of switching to the first treatment mode is performed.

Accordingly, the grasping treatment device 1 having the configuration described above provides the following advantageous effects. In the grasping treatment device 1, the second contraction amount x2 of the coil spring (elastic member) 126 in the second treatment mode is greater than the first contraction amount x1 of the coil spring (elastic member) 126 in the first treatment mode. Thus, the second elastic force k0(x0+x2) acting on the movable portion (the movable cylindrical member 46 and the inner pipe 77) from the elastic member unit 125 in the second treatment mode is greater than the first elastic force k0(x0+x1) acting on the movable portion (46 and 77) from the elastic member unit 125 in the first treatment mode. Therefore, in the second treatment mode, the grasping target is grasped between the first electrode portion 23 and the jaw 42 with the second grasping force F2 greater than the first grasping force F1 in the first treatment mode. Thus, the reformation of the living tissue (grasping target) with the high-frequency current is more accelerated in the second treatment mode than in the first treatment mode. Therefore, the performance of the coagulation of the grasping target with the high-frequency current is improved, so that deterioration in the performance of the coagulation of the grasping target can be prevented in the second treatment mode, which does not use the ultrasonic vibration. Consequently, the grasping target (living tissue) can be stably sealed in the second treatment mode, which does not use the ultrasonic vibration.

Modification of Second Embodiment

The configuration to electrically disconnect the first treatment mode input button 57A from the controller 10 in the second treatment mode is not limited to the second embodiment. For example, the configuration to electrically disconnect the first treatment mode input button 57A from the controller 10 in the second treatment mode may be applied to the grasping treatment device 1 according the first embodiment. That is, it is only necessary to provide the electric disconnection portion (153) which is configured to electrically disconnect the first treatment mode input button 57A from the controller 10 so that the electric signal is not transmitted to the controller 10 from the first treatment mode input button 57A in the second treatment mode regardless of whether the input operation of switching to the first treatment mode is performed.

Third Embodiment

Now, a third embodiment of the present invention is described with reference to FIG. 22 and FIG. 23. In the third embodiment, the configuration according to the embodiments described above is modified as below. The same parts as those in the embodiments, described above are provided with the same reference signs, and are not described.

Figure 23:
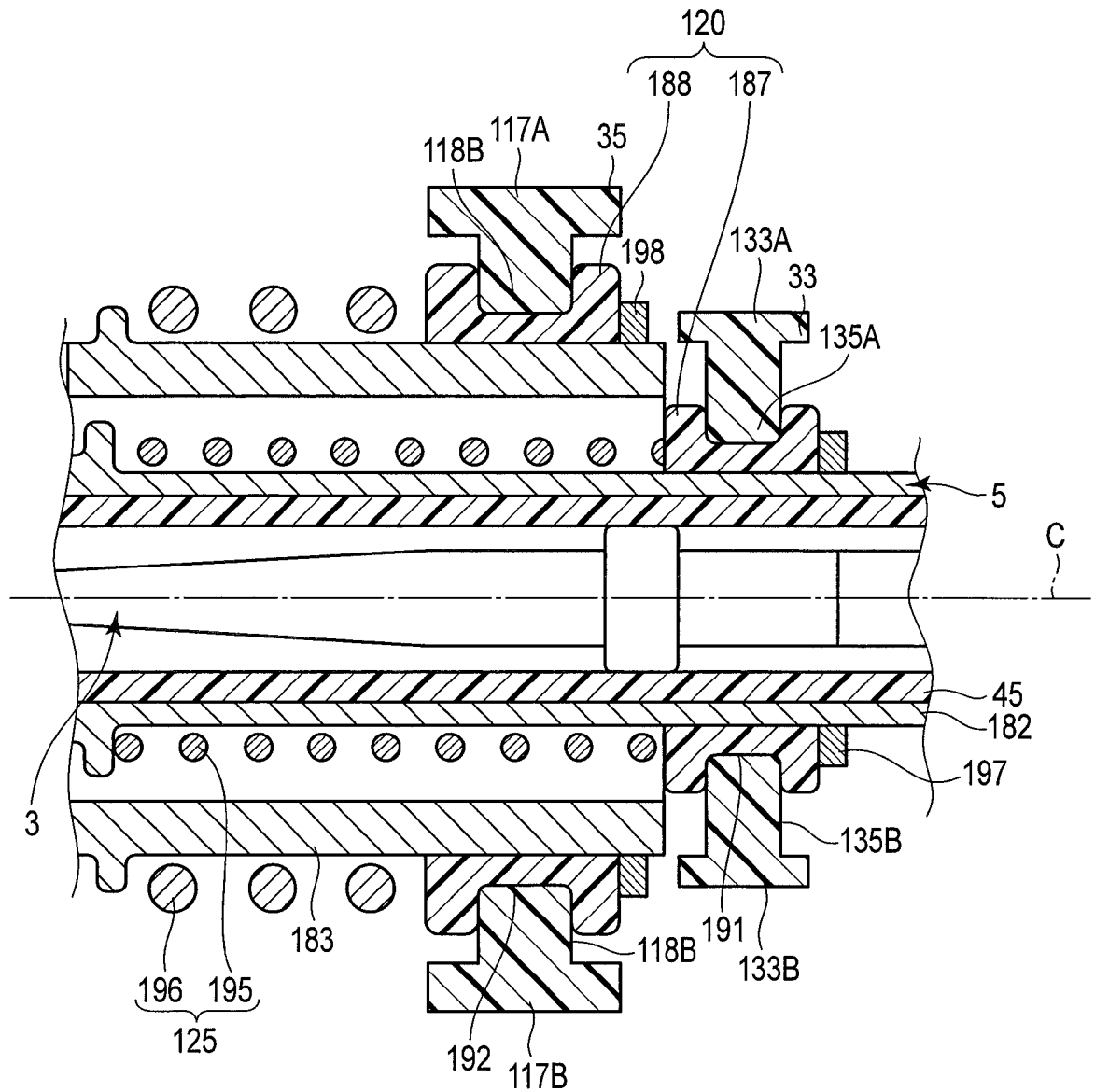
FIG. 23 is a schematic sectional view showing, in a section different from that in FIG. 22, the coupling configuration between the handle unit and the sheath according to the third embodiment.

FIG. 22 and FIG. 23 are diagrams showing a coupling configuration between a handle unit 4 and a sheath 5 according to the present embodiment. As shown in FIG. 22 and FIG. 23, the handle unit 4 includes a first movable handle 33 and a second movable handle 35, as in the first embodiment. The first movable handle 33 and the second movable handle 35 rotate relative to the cylindrical case 31 around the support pin 111. That is, the first movable handle 33 and the second movable handle 35 have the same rotation axis R0.

As in the modification of the first embodiment, arms 133A and 133B are provided in the first movable handle 33. The arm 133A is provided with an engaging protrusion 135A, and the arm 133B is provided with an engaging protrusion 135B. As in the first embodiment, arms 117A and 117B are provided in the second movable handle 35. The arm 117A is provided with an engaging protrusion 118A, and the arm 117B is provided with an engaging protrusion 118B. Only one stopper portion 181 is provided in the fixed handle 32. The first movable handle 33 and the second movable handle 35 can be closed relative to the fixed handle 32 until the first movable handle 33 and the second movable handle 35 abut on the stopper portion 181.

Instead of the movable cylindrical member 46, a first movable cylindrical member 182 and a second movable cylindrical member 183 are provided in the sheath 5. The first movable cylindrical member 182 is provided with through-holes 185A and 185B that are located apart from each other in the directions around the longitudinal axis. Each of the through-holes 185A and 185B is formed into the shape of a long hole along the longitudinal axis C, and passes through the first movable cylindrical member 182 in the diametrical directions. The second movable cylindrical member 183 is provided with through-holes 186A and 186B that are located apart from each other in the directions around the longitudinal axis. Each of the through-holes 186A and 186B is formed into the shape of a long hole along the longitudinal axis C, and passes through the second movable cylindrical member 183 in the diametrical directions.

An engaging pin 47A of a rotational operation knob 37 is inserted through the through-hole 185A and the through-hole 186A, and is engaged with an engaging depression 49A. An engaging pin 47B is inserted through the through-hole 185B and the through-hole 186B, and is engaged with an engaging depression 49B. When each of the engaging pins 47A and 47B is inserted through the corresponding through-hole 185A or 185B, the first movable cylindrical member 182 and the rotational operation knob 37 are regulated unrotatably relative to each other in the directions around the longitudinal axis. When each of the engaging pins 47A and 47B is inserted through the corresponding through-hole 186A or 186B, the second movable cylindrical member 183 and the rotational operation knob 37 are regulated unrotatably relative to each other in the directions around the longitudinal axis. However, the first movable cylindrical member 182 and the second movable cylindrical member 183 are movable relative to the rotational operation knob 37 and the connection cylindrical member 45 along the longitudinal axis C. In this configuration, the first movable cylindrical member 182 and the second movable cylindrical member 183 are rotatable relative to the cylindrical case 31 in the directions around the longitudinal axis together with the rotational operation knob 37 and the connection cylindrical member 45. Moreover, the first movable cylindrical member 182 and the second movable cylindrical member 183 are movable relative to a probe 3 and the handle unit 4 along the longitudinal axis C.

The first movable cylindrical member 182 is made of an electrically conducting material, and is coupled to a vibrator case 11. When the first movable cylindrical member 182 (sheath 5) is coupled to the vibrator case 11, a distal portion of a fourth electric conducting portion 63D of the vibrator case 11 comes into electric contact with the first movable cylindrical member 182. Thus, a high-frequency current is transmitted between a high-frequency current supplier 9 and the first movable cylindrical member 182 of the sheath 5 via the electric signal line 69 and the fourth electric conducting portion 63D.

The first movable cylindrical member 182 and the second movable cylindrical member 183 are fixed to each other via a connection pin 79. The first movable cylindrical member 182 is fixed to an inner pipe 77 via a connection member 78 and the connection pin 79. In the present embodiment, the inner pipe 77 is movable relative to the handle unit 4 and the probe 3 along the longitudinal axis C together with the first movable cylindrical member 182 and the second movable cylindrical member 183. Here, the first movable cylindrical member 182, the second movable cylindrical member 183, and the inner pipe 77 serve as a movable portion which is movable relative to the probe 3 along the longitudinal axis C. A high-frequency current is transmitted to the inner pipe 77 from the first movable cylindrical member 182 through the connection member 78 and the connection pin 79.

A slider portion 120 includes a first slider 187 provided on an outer peripheral portion of the first movable cylindrical member 182, and a second slider 188 provided on an outer peripheral portion of the second movable cylindrical member 183. In the first slider 187, an engaging groove 191 which is depressed toward the inner peripheral direction is formed along the directions around the longitudinal axis. When the engaging protrusions 135A and 135B are engaged with the engaging groove 191, the first movable handle 33 is attached to the first slider 187. The first slider 187 is rotatable relative to the first movable handle 33 and the cylindrical case 31 in the directions around the longitudinal axis together with the first movable cylindrical member 182 (sheath 5). In the second slider 188, an engaging groove 192 which is depressed toward the inner peripheral direction is formed along the directions around the longitudinal axis. When the engaging protrusions 118A and 118B are engaged with the engaging groove 192, the second movable handle 35 is attached to the second slider 188. The second slider 188 is rotatable relative to the second movable handle 35 and the cylindrical case 31 in the directions around the longitudinal axis together with the second movable cylindrical member 183 (sheath 5).

The elastic member unit 125 includes a first coil spring 195 which is a first elastic member, and a second coil spring 196 which is a second elastic member. The first slider 187 is connected to the first movable cylindrical member 182 via the first coil spring 195. The second slider 188 is connected to the second movable cylindrical member 183 via the second coil spring 196.

In the noncontact state in which a jaw 42 is out of contact with a grasping target, the first coil spring 195 is attached between the first movable cylindrical member 182 and the first slider 187 in a reference state in which first coil spring 195 has contracted from the natural state by the contraction amount x0. First coil spring 195 has a first elastic constant k1. Thus, in the noncontact state in which the jaw 42 is out of contact with the grasping target, elastic force k1x0 acts on the first movable cylindrical member 182 (movable portion) from the first coil spring 195. A first stopper portion 197 is provided to the proximal direction side of the first slider 187. The movement of the first slider 187 toward the proximal direction is regulated by the first stopper portion 197.

In the noncontact state in which the jaw 42 is out of contact with the grasping target, the second coil spring 196 is attached between the second movable cylindrical member 183 and the second slider 188 in the reference state in which the second coil spring 196 has contracted from the natural state by the contraction amount x0. The second coil spring 196 has a second elastic constant k2 higher than the first elastic constant k1, and the second coil spring 196 is different in kind from the first coil spring 195. Thus, in the noncontact state in which the jaw 42 is out of contact with the grasping target, elastic force k2x0 acts on the second movable cylindrical member 183 (movable portion) from the second coil spring 196. A second stopper portion 198 is provided to the proximal direction side of the second slider 188. The movement of the second slider 188 toward the proximal direction is regulated by the second stopper portion 198.

As described above, in the noncontact state in which the jaw 42 is out of contact with the grasping target, the elastic force k1x0 acts on the first movable cylindrical member 182 (movable portion) from the first coil spring 195, and the elastic force k2x0 acts on the second movable cylindrical member 183 (movable portion) from the second coil spring 196. Therefore, in the noncontact state in which the jaw 42 is out of contact with the grasping target, elastic force (k1+k2)x0 acts on the movable portion including the first movable cylindrical member 182 and the second movable cylindrical member 183 from the elastic member unit 125.

Now, the functions of the grasping treatment device 1 according to the present embodiment are described. When the grasping target is grasped between the first electrode portion 23 and the jaw 42 in the first treatment mode, the first movable handle 33 is operated to close the jaw 42. When the first movable handle 33 is closed relative to the fixed handle 32, the first slider 187 moves toward the distal direction along the longitudinal axis C together with the movable portion (the first movable cylindrical member 182, the second movable cylindrical member 183, and the inner pipe 77) and the second slider 188. In this case, the noncontact state in which the jaw 42 is out of contact with the grasping target is kept until the jaw 42 comes into contact with the grasping target, so that first coil spring 195 does not contract from the reference state. Thus, the elastic force acting on the first movable cylindrical member 182 from the first coil spring 195 does not change from k1x0. Therefore, the elastic force acting on the movable portion from the elastic member unit 125 does not change from $(k1+k2)x0$. The jaw 42 is closed relative to the first electrode portion 23 by the movement of the first movable cylindrical member 182, the second movable cylindrical member 183, and the inner pipe 77 toward the distal direction.

When the jaw 42 comes into the contact state to contact the grasping target, the first movable handle 33 is further closed relative to the fixed handle 32 so that the first slider 187 moves relative to the first movable cylindrical member 182 (movable portion) toward the distal direction. Thus, the first coil spring 195 further contracts from the reference state. Therefore, elastic force $k1(x0+x')$ greater than the elastic force $k1x0$ in the reference state acts on the first movable cylindrical member 182 (movable portion) from the first coil spring 195, and the movable portion (the first movable cylindrical member 182, the second movable cylindrical member 183, and the inner pipe 77) further moves toward the distal direction. As a result, the jaw 42 which has come into contact with the grasping target is further closed relative to the first electrode portion 23, and the grasping force to grasp the grasping target between the jaw 42 and the first electrode portion 23 is increased.

If the first movable handle 33 is closed until the first movable handle 33 abuts on the stopper portion 181, the first coil spring 195 contracts from the reference state in a contraction amount $x'0$. Thus, elastic force $k1(x0+x'0)$ acts on the first movable cylindrical member 182 (movable portion) from the first coil spring 195. Here, in the first treatment mode, the second slider 188 does not move relative to the second movable cylindrical member 183, so that the second coil spring 196 does not contract from the reference state. Thus, in the first treatment mode, the elastic force acting on the second movable cylindrical member 183 (movable portion) from the second coil spring 196 does not change from $k2x0$. Therefore, when the first movable handle 33 is in abutment with the stopper portion 181, first elastic force $(k1+k2)x0+k1x'0$ acts on the movable portion (the first movable cylindrical member 182, the second movable cylindrical member 183, and the inner pipe 77) from the elastic member unit 125. As a result, the grasping target is grasped between the first electrode portion 23 and the jaw 42 with the first grasping force F1.

When the grasping target is grasped between the first electrode portion 23 and the jaw 42 in the second treatment mode, the second movable handle 35 is operated to close the jaw 42. When the second movable handle 35 is closed relative to the fixed handle 32, the second slider 188 moves toward the distal direction along the longitudinal axis C together with the movable portion (the first movable cylindrical member 182, the second movable cylindrical member 183, and the inner pipe 77) and the first slider 187. In this case, the noncontact state in which the jaw 42 is out of contact with the grasping target is kept until the jaw 42 comes into contact with the grasping target, so that the second coil spring 196 does not contract from the reference state. Thus, the elastic force acting on the second movable cylindrical member 183 from the second coil spring 196 does not change from $k2x0$. Therefore, the elastic force acting on the movable portion from the elastic member unit 125 does not change from $(k1+k2)x0$. The jaw 42 is closed relative to the first electrode portion 23 by the movement of the first movable cylindrical member 182, the second movable cylindrical member 183, and the inner pipe 77 toward the distal direction.

When the jaw 42 comes into the contact state to contact the grasping target, the second movable handle 35 is further closed relative to the fixed handle 32 so that the second slider 188 moves relative to the second movable cylindrical member 183 (movable portion) toward the distal direction. Thus, the second coil spring 196 further contracts from the reference state. Therefore, elastic force $k2(x0+x')$ greater than the elastic force $k2x0$ in the reference state acts on the second movable cylindrical member 183 (movable portion) from the second coil spring 196, and the movable portion (the first movable cylindrical member 182, the second movable cylindrical member 183, and the inner pipe 77) further moves toward the distal direction. As a result, the jaw 42 which has come into contact with the grasping target is further closed relative to the first electrode portion 23, and the grasping force to grasp the grasping target between the jaw 42 and the first electrode portion 23 is increased.

If the second movable handle 35 is closed until the second movable handle 35 abuts on the stopper portion 181, the second coil spring 196 contracts from the reference state by the contraction amount $x'0$. Thus, elastic force $k2(x0+x'0)$ acts on the second movable cylindrical member 183 (movable portion) from the second coil spring 196. Here, in the second treatment mode, the first slider 187 does not move relative to the first movable cylindrical member 182, so that the first coil spring 195 does not contract from the reference state. Thus, in the second treatment mode, the elastic force acting on the first movable cylindrical member 182 (movable portion) from the first coil spring 195 does not change from $k1x0$. Therefore, when the second movable handle 35 is in abutment with the stopper portion 181, second elastic force $(k1+k2)x0+k2x'0$ acts on the movable portion (the first movable cylindrical member 182, the second movable cylindrical member 183, and the inner pipe 77) from the elastic member unit 125. Here, the second elastic constant k2 is higher than the first elastic constant k1. Thus, the second elastic force $(k1+k2)x0+k2x'0$ is greater than the first elastic force $(k1+k2)x0+k1x'0$ in the first treatment mode. As a result, the grasping target is grasped between the first electrode portion 23 and the jaw 42 with the second grasping force F2 greater than the first grasping force F1.

As described above, in the present embodiment, the fixed handle 32, the first movable handle 33, and the second movable handle 35 serve as a contractible member converter configured to convert a kind of elastic member (195, 196) to be contracted between the first treatment mode and the second treatment mode. Owing to the contractible member converter, the first coil spring (first elastic member) 195 having the first elastic constant k1 contracts in the first treatment mode, and the second coil spring (second elastic member) 196 having the second elastic constant k2 higher than the first elastic constant k1 contracts in the second treatment mode. Thus, the fixed handle 32, the first movable handle 33, and the second movable handle 35 serve as an elastic force converter configured to convert an elastic force so that the second elastic force $(k1+k2)x0+k2x'0$ acting on the movable portion (the first movable cylindrical member 182, the second movable cylindrical member 183, and the inner pipe 77) from the elastic member unit 125 in the second treatment mode is greater than the first elastic force $(k1+k2)x0+k1x'0$ acting on the movable portion (182, 183, and 77) from the elastic member unit 125 in the first treatment mode. Therefore, the fixed handle 32, the first movable handle 33, and the second movable handle 35 serve as a grasping force converting unit configured to convert a grasping force so that the second grasping force F2 between the first electrode portion 23 and the jaw 42 in the second treatment mode is greater than the first grasping force F1 between the first electrode portion 23 and the jaw 42 in the first treatment mode.

Accordingly, the grasping treatment device 1 having the configuration described above provides the following advantageous effects. In the grasping treatment device 1, the kind of elastic member (195, 196) to be contracted is converted between the first treatment mode and the second treatment mode. As a result, the first coil spring (first elastic member) 195 having the first elastic constant k1 contracts in the first treatment mode, and the second coil spring (second elastic member) 196 having the second elastic constant k2 higher than the first elastic constant k1 contracts in the second treatment mode. Thus, the second elastic force $(k1+k2)x0+k2x'0$ acting on the movable portion (the first movable cylindrical member 182, the second movable cylindrical member 183, and the inner pipe 77) from the elastic member unit 125 in the second treatment mode is greater than the first elastic force $(k1+k2)x0+k1x'0$ acting on the movable portion (182, 183, and 77) from the elastic member unit 125 in the first treatment mode. Therefore, in the second treatment mode, the grasping target is grasped between the first electrode portion 23 and the jaw 42 with the second grasping force F2 greater than the first grasping force F1 in the first treatment mode. Thus, the reformation of the living tissue (grasping target) with the high-frequency current is more accelerated in the second treatment mode than in the first treatment mode. Therefore, the performance of the coagulation of the grasping target with the high-frequency current is improved, so that deterioration in the performance of the coagulation of the grasping target can be prevented in the second treatment mode which does not use the ultrasonic vibration. Consequently, the grasping target (living tissue) can be stably sealed in the second treatment mode which does not use the ultrasonic vibration.

Modification of Third Embodiment

Figure 25:
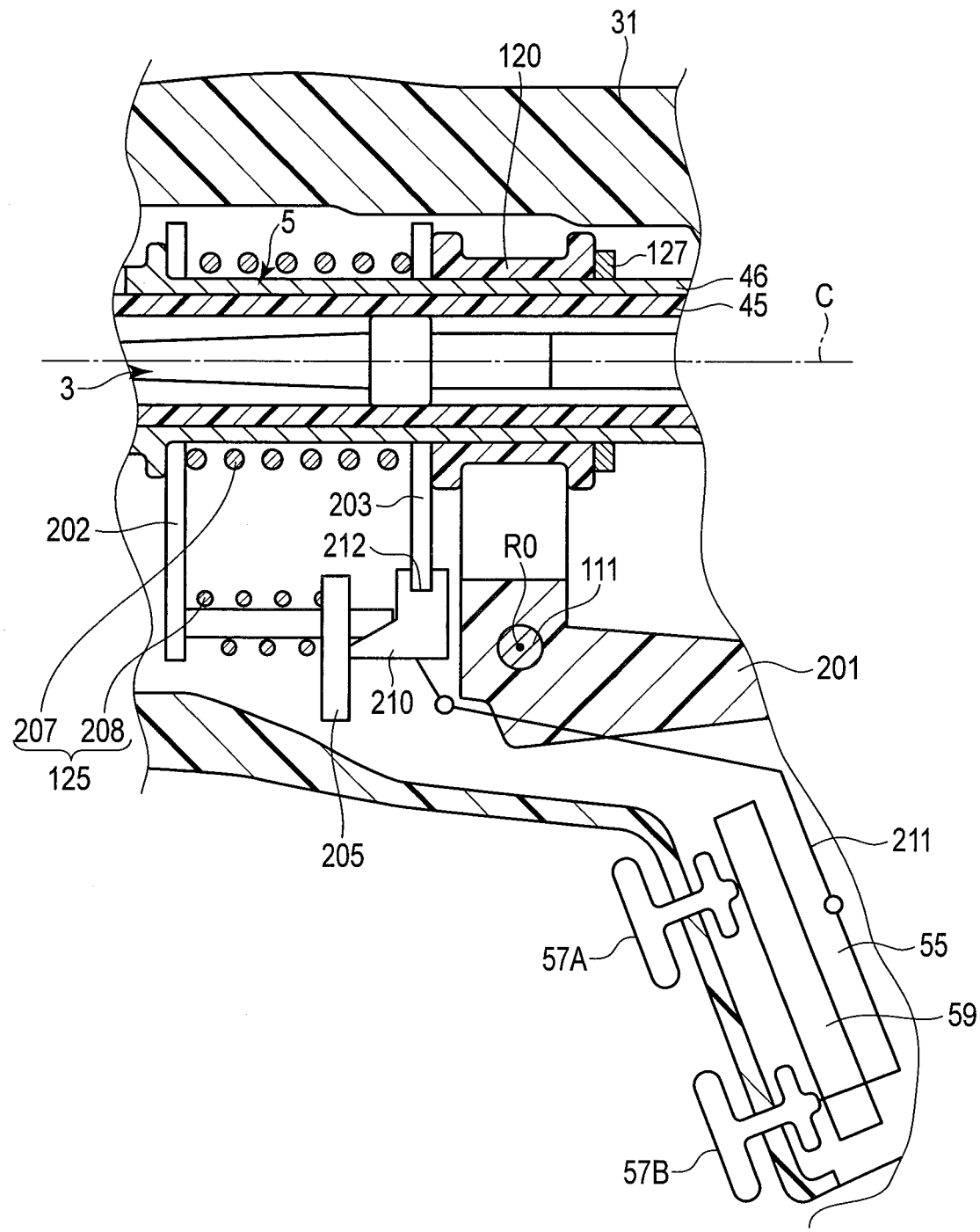
FIG. 25 is a schematic sectional view showing the internal configuration of the handle unit according to the modification of the third embodiment in the second treatment mode.

While the kind of elastic member (195, 196) to be contracted is converted between the first treatment mode and the second treatment mode in the third embodiment, the present invention is not limited to this. For example, as in a modification shown in FIG. 24 and FIG. 25, the number of the elastic members to be contracted may be converted between the first treatment mode and the second treatment mode. FIG. 24 shows the first treatment mode. FIG. 25 shows the second treatment mode.

As shown in FIG. 24 and FIG. 25, the handle unit 4 according to the present modification includes a cylindrical case 31, a fixed handle 32, and a switch arrangement portion 55, as in the third embodiment. A stopper portion 181 is provided in the fixed handle 32. However, in the present modification, only one movable handle 201 configured to open or close relative to the fixed handle 32 is provided. In the present modification as well, the movable handle 201 is configured to open or close relative to the fixed handle 32 substantially parallel with the longitudinal axis C, as in the third embodiment. The movable handle 201 is attached to a slider portion 120 in the same manner as the second movable handle 35 according to the first embodiment.

In the present modification, a movable cylindrical member 46 is provided, as in the first embodiment. The slider portion 120 is located on the outer peripheral portion of the movable cylindrical member 46. An intermediary member 202 is fixed to the movable cylindrical member 46 (movable portion). An intermediary member 203 is fixed to the slider portion 120. A block 205 is attached to the intermediary member 202. The block 205 is movable relative to the intermediary member 202 along the longitudinal axis C.

The intermediary member 202 and the intermediary member 203 are connected via a first coil spring 207 which is a first elastic member. The first coil spring 207 has a first elastic constant k'1. The block 205 and the intermediary member 202 are connected via a second coil spring 208 which is a second elastic member. The second coil spring 208 has a second elastic constant k'2. The first elastic constant k'1 and the second elastic constant k'2 may have the same value or different values. Each of the first coil spring 207 and the second coil spring 208 is provided in a reference state in which each of these coil springs is contracted from the natural state by the contraction amount x0. Therefore, in the noncontact state in which the jaw 42 is out of contact with the grasping target, elastic force $(k'1+k'2)x0$ acts on the movable portion (the movable cylindrical member 46 and the inner pipe 77) from the elastic member unit 125.

An engaging member 210 is provided inside the cylindrical case 31. The engaging member 210 is coupled to a second treatment mode input button 57B via a link 211. If the second treatment mode input button 57B is pressed, the engaging member 210 is pressed toward the intermediary member 203 via the link 211. The engaging member 210 is provided with an engaging groove 212 which is engaged with the intermediary member 203. If the intermediary member 203 is engaged with the engaging groove 212, the engaging member 210 connects between the intermediary member 203 and the block 205. Thus, force can be transmitted to the block 205 from the slider portion 120 via the intermediary member 203 and the engaging member 210. The configuration to engage the engaging member 210 with the intermediary member 203 is not limited to the above-mentioned link 211. For example, a movement unit which is driven in accordance with a signal of indicating that the second treatment mode input button 57B is pressed may be provided. In this case, the engaging member 210 is engaged with the intermediary member 203 by directly moving the engaging member 210 in accordance with the signal without providing multiple members in between.

When the grasping target is grasped between the first electrode portion 23 and the jaw 42, the movable handle 201 is operated to close the jaw 42. In the first treatment mode, the second treatment mode input button 57B is not pressed. Thus, the engaging member 210 does not connect between the intermediary member 203 and the block 205, and no force is transmitted to the block 205 from the slider portion 120.

If the movable handle 201 is closed relative to the fixed handle 32 in the contact state in which the jaw 42 is in contact with the grasping target, the slider portion 120 moves relative to the movable cylindrical member 46 (movable portion) toward the distal direction. In this case, since no force is transmitted to the block 205 from the slider portion 120, the first coil spring 207 alone contracts from the reference state, and the second coil spring 208 does not contract from the reference state.

If the movable handle 201 is closed until the movable handle 201 abuts on the stopper portion 181, the first coil spring 207 contracts from the reference state by the contraction amount x'0. Thus, elastic force $k'1(x0+x'0)$ acts on the movable cylindrical member 46 (movable portion) from the first coil spring 207. In this condition, a first treatment mode input button 57A is pressed. Here, since no force is transmitted to the block 205 from the slider portion 120 in the first treatment mode, the second coil spring 208 does not contract from the reference state. Thus, in the first treatment mode, the elastic force acting on the movable cylindrical member 46 (movable portion) from the second coil spring 208 does not change from $k'2x0$. Therefore, when the movable handle 201 is in abutment with the stopper portion 181, first elastic force $(k'1+k'2)x0+k'1x'0$ acts on the movable portion (the movable cylindrical member 46 and the inner pipe 77) from the elastic member unit 125. As a result, the grasping target is grasped between the first electrode portion 23 and the jaw 42 with the first grasping force F1.

In the second treatment mode, the movable handle 201 is closed relative to the fixed handle 32 in the contact state in which the jaw 42 is in contact with the grasping target, and the slider portion 120 thereby moves relative to the movable cylindrical member 46 (movable portion) toward the distal direction. If the movable handle 201 is closed until the movable handle 201 abuts on the stopper portion 181, the first coil spring 207 contracts from the reference state by the contraction amount x'0. Thus, the elastic force k'1(x0+x'0) acts on the movable cylindrical member 46 (movable portion) from the first coil spring 207. Here, in the second treatment mode, the second treatment mode input button 57B is pressed in this condition. Thus, the engaging member 210 connects between the intermediary member 203 and the block 205, and force can be transmitted to the block 205 from the slider portion 120. Therefore, in the second treatment mode, the movable cylindrical member 46 (movable portion) and the slider portion 120 are connected by the second coil spring 208 which is a second elastic member in addition to the first coil spring 207. That is, in the second treatment mode, the second coil spring 208 is disposed parallel to the first coil spring 207. In this case, since force is transmitted to the block 205 from the slider portion 120, not only the first coil spring 207 but also the second coil spring 208 contracts from the reference state.

In the second treatment mode, since force is transmitted to the block 205 from the slider portion 120, the second coil spring 208 also contracts from the reference state by the contraction amount x'0. Thus, in the second treatment mode, the elastic force k'2(x0+x'0) acts on the movable cylindrical member 46 (movable portion) from the second coil spring 208. Therefore, when the movable handle 201 is in abutment with the stopper portion 181, second elastic force (k'1+k'2)(x0+x'0) greater than the first elastic force (k'1+k'2)x0+k'1x'0 acts on the movable portion (the movable cylindrical member 46 and the inner pipe 77) from the elastic member unit 125. As a result, the grasping target is grasped between the first electrode portion 23 and the jaw 42 with the second grasping force F2 greater than the first grasping force F1.

As described above, in the present modification, the second treatment mode input button 57B serves as a connection state changeover portion configured to change the connection state between the movable portion (the movable cylindrical member 46 and the inner pipe 77) and the slider portion 120. Owing to the connection state changeover portion (57B), the movable portion (46 and 77) and the slider portion 120 are connected by the first coil spring 207 in the first treatment mode. In the second treatment mode, the movable portion (46 and 77) and the slider portion 120 are connected not only by the first coil spring 207 but also by the second coil spring 208 disposed parallel to the first coil spring 207. That is, the second treatment mode input button 57B serves as a contractible member converter configured to convert the number of the elastic members (195, 196) to be contracted between the first treatment mode and the second treatment mode. Owing to the contractible member converter, the first coil spring (first elastic member) 207 contracts in the first treatment mode, and the second coil spring (second elastic member) 208 contracts in addition to the first coil spring 207 in the second treatment mode. Thus, the second treatment mode input button 57B serves as an elastic force converter configured to convert an elastic force so that the second elastic force (k'1+k'2)(x0+k'0) acting on the movable portion (the movable cylindrical member 46 and the inner pipe 77) from the elastic member unit 125 in the second treatment mode is greater than the first elastic force (k'1+k'2)x0+k'1x'0 acting on the movable portion (46 and 77) from the elastic member unit 125 in the first treatment mode. Therefore, the second treatment mode input button 57B serves as a grasping force converting unit configured to convert a grasping force so that the second grasping force F2 between the first electrode portion 23 and the jaw 42 in the second treatment mode is greater than the first grasping force F1 between the first electrode portion 23 and the jaw 42 in the first treatment mode.

Fourth Embodiment

Now, a fourth embodiment of the present invention is described with reference to FIG. 26 to FIG. 28. In the fourth embodiment, the configuration according to the embodiments described above is modified as below. The same parts as those in the embodiments described above are provided with the same reference signs, and are not described.

Figure 26:
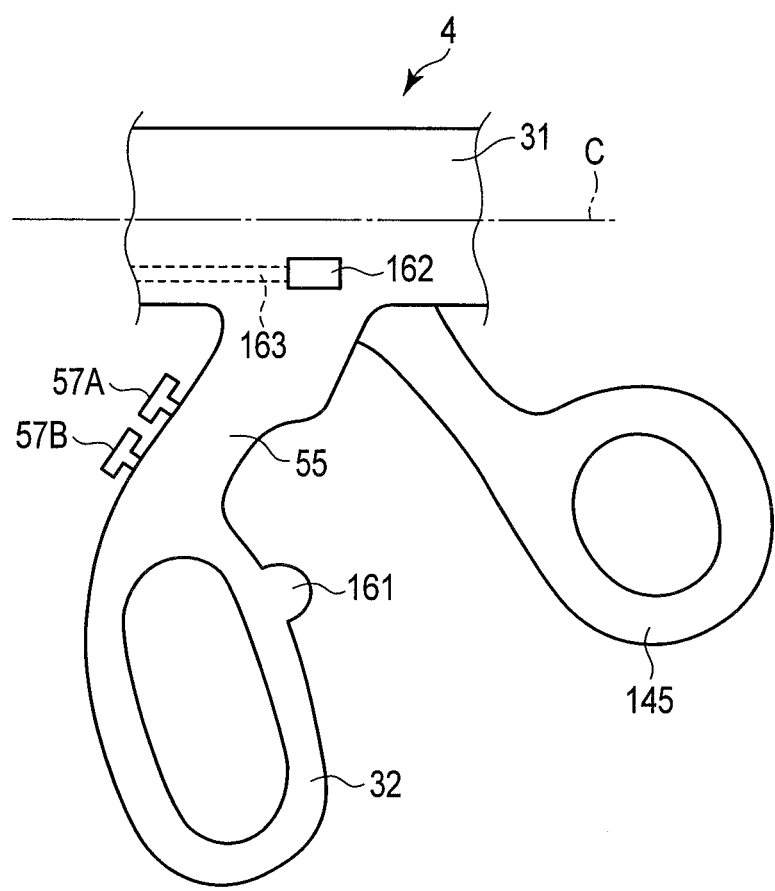
FIG. 26 is a schematic view showing the configuration of a handle unit of a grasping treatment device according to a fourth embodiment of the present invention.

FIG. 26 is a diagram showing the configuration of a handle unit 4 of a grasping treatment device 1 according to the present embodiment. As shown in FIG. 26, the handle unit 4 of the grasping treatment device 1 includes a fixed handle 32 and a movable handle 145, as in the second embodiment. A stopper portion 161 is provided in the fixed handle 32. The movable handle 145 can be closed relative to the fixed handle 32 until the movable handle 145 abuts on the stopper portion 161. The handle unit 4 also includes a member position changeover lever 162 which is a member position changeover portion. The member position changeover lever 162 is made of an insulating material, and is movable relative to a cylindrical case 31 along the longitudinal axis C.

The movable handle 145 is attached to a slider portion 120. In the noncontact state in which a jaw 42 is out of contact with the grasping target, a coil spring 126 does not contract from the reference state. Thus, the elastic force acting on a movable cylindrical member 46 and an inner pipe 77 from the coil spring 126 does not change from k0x0. The jaw 42 is closed relative to a first electrode portion 23 by the movement of the movable cylindrical member 46 and the inner pipe 77 toward the distal direction.

In the contact state in which the jaw 42 is in contact with the grasping target, the slider portion 120 moves relative to the movable cylindrical member 46, and the coil spring 126 contracts. If the movable handle 145 is closed until the movable handle 145 abuts on the stopper portion 161, the coil spring 126 contracts by a contraction amount x3. Thus, the elastic force k0(x0+x3) acts on the movable portion (the movable cylindrical member 46 and the inner pipe 77) from the coil spring 126 of an elastic member unit 125.

Figure 28:
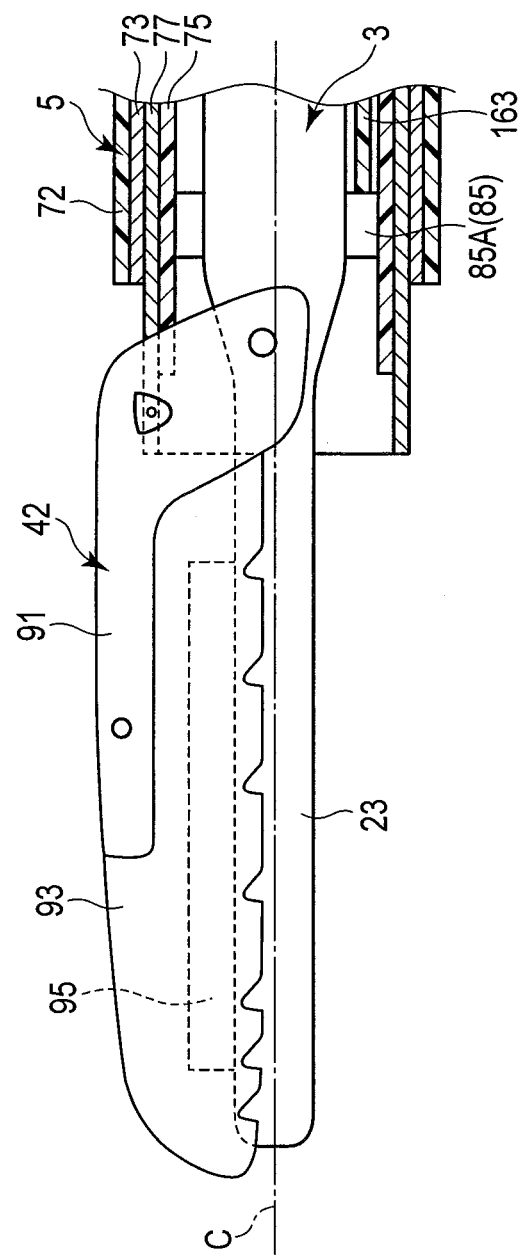
FIG. 28 is a partly sectional schematic view showing the configurations of the distal portion of the probe, the distal portion of the sheath, and the jaw according to the fourth embodiment in the second treatment mode.

FIG. 27 and FIG. 28 are diagrams showing a distal portion of a probe 3, a distal portion of a sheath 5, and the jaw 42. FIG. 27 shows the first treatment mode. FIG. 28 shows the second treatment mode. As shown in FIG. 27 and FIG. 28, a support member 85 which supports the probe between the sheath 5 and the probe 3 includes a most-distal support member 85A which is the support member 85 provided on the most distally among the support member 85. The most-distal support member 85A is coupled to the member position changeover lever 162 via an intermediary portion 163 made of an insulating material. The intermediary portion 163 extends along the longitudinal axis C between an inner tube 75 (sheath 5) and the probe 3. The most-distal support member 85A is movable along the longitudinal axis C relative to the sheath 5 and the probe 3 together with the intermediary portion 163.

The most-distal support member 85A is movable relative to the sheath 5 and the probe 3 between a first member position (see FIG. 27) and a second member position (see FIG. 28) located to the distal direction side of the first member position. The first member position corresponds to, for example, a node position of the ultrasonic vibration located on the second distally among node positions. The second member position corresponds to, for example, a node position of the ultrasonic vibration located on the most distally among the node positions. The most-distal support member 85A is moved between the first member position and the second member position by a changeover operation in the member position changeover lever 162.

Now, the functions of the grasping treatment device 1 according to the present embodiment are described. When the grasping target is grasped between the first electrode portion 23 and the jaw 42 in the first treatment mode, the most-distal support member 85A is moved to the first member position by the changeover operation in the member position changeover lever 162. The movable handle 145 is operated to close the jaw 42, and the movable handle 145 is closed until the movable handle 145 abuts on the stopper portion 161. In this case, the elastic force k0(x0+x3) acts on the movable portion (the movable cylindrical member 46 and the inner pipe 77) from the coil spring 126. Since the most-distal support member 85A is located at the first member position, first press force S1 acts on the grasping target from the first electrode portion 23. Therefore, the grasping target is grasped between the first electrode portion 23 and the jaw 42 with the first grasping force F1.

When the grasping target is grasped between the first electrode portion 23 and the jaw 42 in the second treatment mode, the most-distal support member 85A is moved to the second member position by the changeover operation in the member position changeover lever 162. The movable handle 145 is operated to close the jaw 42, and the movable handle 145 is closed until the movable handle 145 abuts on the stopper portion 161. In this case, the elastic force k0(x0+x3) acts on the movable portion (the movable cylindrical member 46 and the inner pipe 77) from the coil spring 126. The most-distal support member 85A is located at the second member position which is located to the distal direction side of the first member position. Thus, second press force S2 greater than the first press force S1 acts on the grasping target from the first electrode portion 23. Therefore, the grasping target is grasped between the first electrode portion 23 and the jaw 42 with the second grasping force F2 greater than the first grasping force F1.

As described above, in the present embodiment, the member position changeover lever 162 serves as a support state converter configured to convert, between the first treatment mode and the second treatment mode, a support state of the probe 3 between the probe 3 and the sheath 5. Owing to the support state converter (162), the second press force S2 acting on the grasping target from the first electrode portion 23 in the second treatment mode is greater than the first press force S1 acting on the grasping target from the first electrode portion 23 in the first treatment mode. Therefore, the member position changeover lever 162 serves as a grasping force converting unit configured to convert a grasping force so that the second grasping force F2 between the first electrode portion 23 and the jaw 42 in the second treatment mode is greater than the first grasping force S1 between the first electrode portion 23 and the jaw 42 in the first treatment mode.

Accordingly, the grasping treatment device 1 having the configuration described above provides the following advantageous effects. In the grasping treatment device 1, the most-distal support member 85A is located at the first member position in the first treatment mode, and the most-distal support member 85A is located at the second member position in the second treatment mode which is located to the distal direction side of the first member position. Thus, the second press force S2 acting on the grasping target from the first electrode portion 23 in the second treatment mode is greater than the first press force S1 acting on the grasping target from the first electrode portion 23 in the first treatment mode. Therefore, in the second treatment mode, the grasping target is grasped between the first electrode portion 23 and the jaw 42 with the second grasping force F2 greater than the first grasping force F1 in the first treatment mode. Thus, the reformation of the living tissue (grasping target) with the high-frequency current is more accelerated in the second treatment mode than in the first treatment mode. Therefore, the performance of the coagulation of the grasping target with the high-frequency current is improved, so that deterioration in the performance of the coagulation of the grasping target can be prevented in the second treatment mode, which does not use the ultrasonic vibration. Consequently, the grasping target (living tissue) can be stably sealed in the second treatment mode, which does not use the ultrasonic vibration.

Modification of Fourth Embodiment

Figure 29:
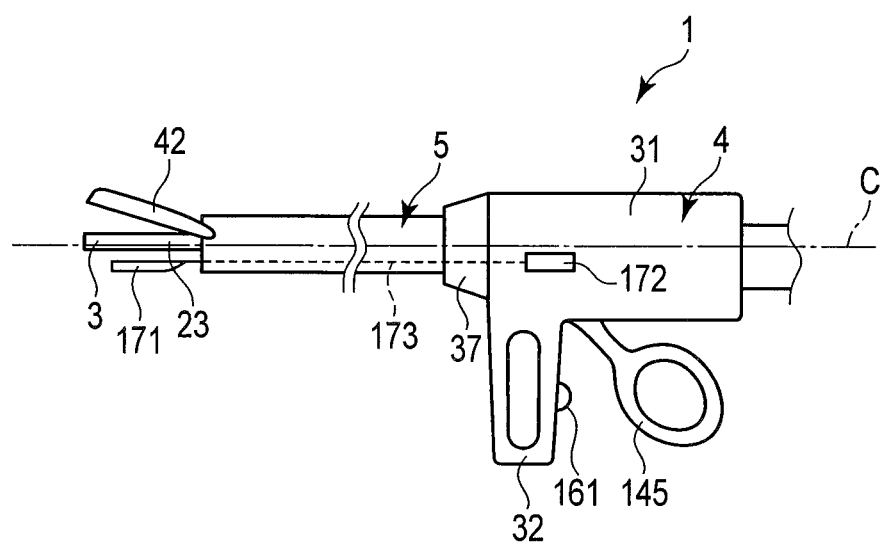
FIG. 29 is a schematic view showing the configuration of the grasping treatment device according to a modification of the fourth embodiment.

While the support state of the probe 3 is converted between the first treatment mode and the second treatment mode by the movement of the most-distal support member 85A in the fourth embodiment, the present invention is not limited to this. For example, as in a modification shown in FIG. 29 to FIG. 31, the most-distal support member 85A may be configured to be immobile. In the present modification, a movement member 171 is provided. A handle unit 4 is provided with a member position changeover switch 172 which is a member position changeover portion. The movement member 171 is coupled to the member position changeover switch 172 via an intermediary portion 173. The intermediary portion 173 extends along the longitudinal axis C between the sheath 5 and the probe 3. The movement member 171, the member position changeover switch 172, and the intermediary portion 173 are made of an insulating material. The position of the most-distal support member 85A corresponds to, for example, a node position of the ultrasonic vibration located on the second distally among node positions.

Figure 30:
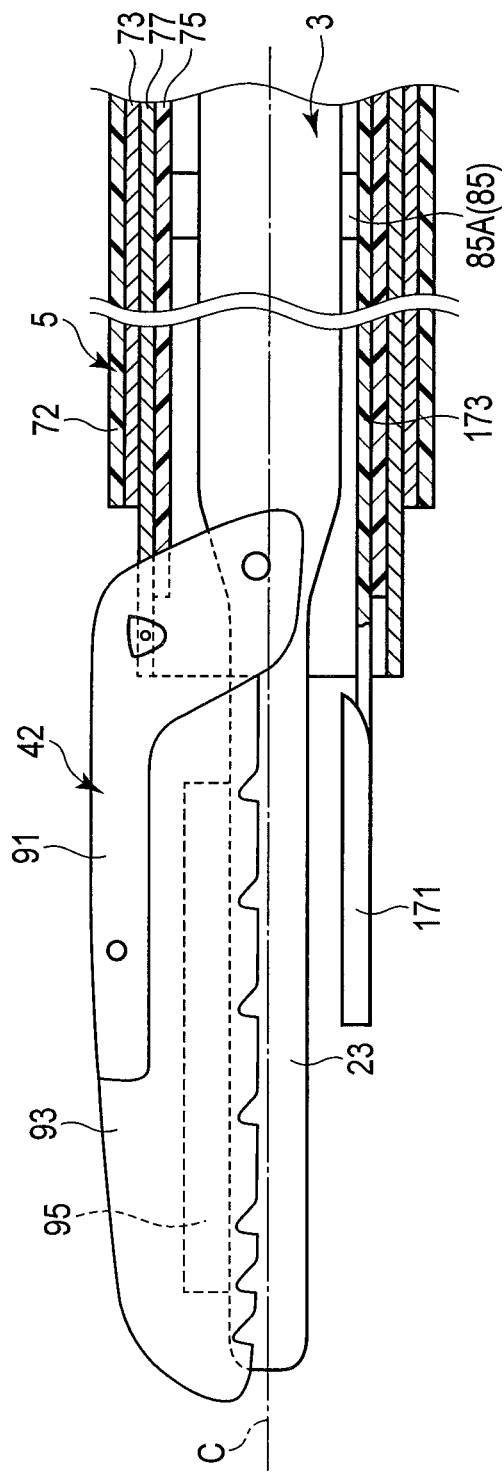
FIG. 30 is a partly sectional schematic view showing the configurations of a distal portion of a probe, a distal portion of a sheath, and a jaw according to the modification of the fourth embodiment in the first treatment mode.

The movement member 171 is moved relative to the sheath 5 and the probe 3 along the longitudinal axis C by a changeover operation in the member position changeover switch 172. As shown in FIG. 30, in the first treatment mode, the movement member 171 is located at the first member position positioned to the distal direction side of the distal end of the sheath 5 by the changeover operation in the member position changeover switch 172. At the first member position, the movement member 171 does not contact the first electrode portion 23. Thus, the probe 3 is not supported in a part located to the distal direction side of the most-distal support member 85A.

Figure 31:
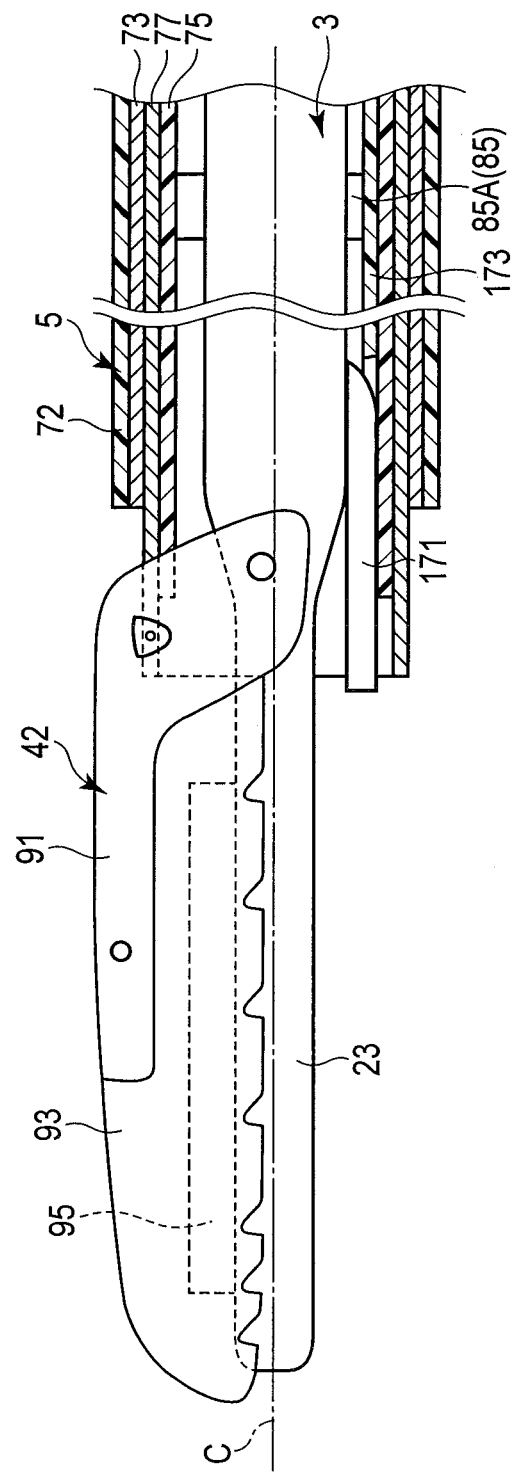
FIG. 31 is a partly sectional schematic view showing the configurations of the distal portion of the probe, the distal portion of the sheath, and the jaw according to the modification of the fourth embodiment in the second treatment mode.

As shown in FIG. 31, in the second treatment mode, the movement member 171 is located at the second member position situated to the proximal direction side of the first member position and situated between the sheath 5 and the probe 3, by the changeover operation in the member position changeover switch 172. At the second member position, the movement member 171 supports the probe 3. The second member position is located to the distal direction of the most-distal support member 85A. That is, in the second treatment mode, the probe 3 is supported at position located to the distal direction of the most-distal support member 85A.

As described above, in the present modification, the member position changeover switch 172 serves as a support state converter configured to convert, between the first treatment mode and the second treatment mode, a support state of the probe 3 between the probe 3 and the sheath 5. Owing to the support state converter (172), the second press force S2 acting on the grasping target from the first electrode portion 23 in the second treatment mode is greater than the first press force S1 acting on the grasping target from the first electrode portion 23 in the first treatment mode. Therefore, the member position changeover switch 172 serves as a grasping force converting unit configured to convert a grasping force so that the second grasping force F2 between the first electrode portion 23 and the jaw 42 in the second treatment mode is greater than the first grasping force F1 between the first electrode portion 23 and the jaw 42 in the first treatment mode.

Fifth Embodiment

Now, a fifth embodiment of the present invention is described with reference to FIG. 32 and FIG. 33. In the fifth embodiment, the configuration according to the embodiments described above is modified as below. The same parts as those in the embodiments described above are provided with the same reference signs, and are not described.

FIG. 32 and FIG. 33 are diagrams showing the configuration of a grasping treatment device 1 according to the present embodiment. FIG. 32 shows the first treatment mode. FIG. 33 shows the second treatment mode. As shown in FIG. 32 and FIG. 33, a handle unit 4 of the grasping treatment device 1 includes a fixed handle 32 and a movable handle 145, as in the fourth embodiment. A stopper portion 161 is provided in the fixed handle 32. The movable handle 145 can be closed relative to the fixed handle 32 until the movable handle 145 abuts on the stopper portion 161. The handle unit 4 also includes a movement position changeover button 221 which is a member position changeover portion. The movement position changeover button 221 is made of an insulating material.

The movable handle 145 is attached to a slider portion 120. In the noncontact state in which a jaw 42 is out of contact with the grasping target, a coil spring 126 does not contract from the reference state. Thus, the elastic force acting on a movable cylindrical member 46 and an inner pipe 77 from the coil spring 126 does not change from k0x0. The jaw 42 is closed relative to a first electrode portion 23 by the movement of the movable cylindrical member 46 and the inner pipe 77 toward the distal direction.

In the contact state in which the jaw 42 is in contact with the grasping target, the slider portion 120 moves relative to the movable cylindrical member 46, and the coil spring 126 contracts. If the movable handle 145 is closed until the movable handle 145 abuts on the stopper portion 161, the coil spring 126 contracts by the contraction amount x3. In this case, the elastic force k0(x0+x3) acts on the movable portion (the movable cylindrical member 46 and the inner pipe 77) from the coil spring 126 of an elastic member unit 125.

A cylindrical movement member 222 is provided to the outer peripheral direction side of the sheath 5. The movement member 222 extends along the longitudinal axis C, and is coupled to the movement position changeover button 221. The movement member 222 is movable relative to the sheath 5 along the longitudinal axis C by a changeover operation in the movement position changeover button 221. The movement member 222 is movable between a first movement position (see FIG. 32) and a second movement position (see FIG. 33).

As shown in FIG. 32, at the first movement position, a distal end of the movement member 222 is located to the proximal direction side of the distal end of the sheath 5. At the first movement position, the movement member 222 is not in contact with the jaw 42. As shown in FIG. 33, at the second movement position, the distal end of the movement member 222 is located to the distal direction side of the distal end of the sheath 5. At the second movement position, the movement member 222 is in contact with the jaw 42. Thus, the jaw 42 is pressed toward the first electrode portion 23 by the movement member 222.

When the grasping target is grasped between the first electrode portion 23 and the jaw 42 in the first treatment mode, the movement member 222 is moved to the first movement position by the operation in the movement position changeover button 221. The movable handle 145 is operated to close the jaw 42, and the movable handle 145 is closed until the movable handle 145 abuts on the stopper portion 161. In this case, the elastic force k0(x0+x3) acts on the movable portion (the movable cylindrical member 46 and the inner pipe 77) from the coil spring 126. Therefore, the grasping target is grasped between the first electrode portion 23 and the jaw 42 with the first grasping force F1.

When the grasping target is grasped between the first electrode portion 23 and the jaw 42 in the second treatment mode, the movement member 222 is moved to the second movement position by the operation in the movement position changeover button 221. The movable handle 145 is operated to close the jaw 42, and the movable handle 145 is closed until the movable handle 145 abuts on the stopper portion 161. In this case, the elastic force k0(x0+x3) acts on the movable portion (the movable cylindrical member 46 and the inner pipe 77) from the coil spring 126. Since the movement member 222 is located at the second movement position, the jaw 42 is pressed toward the first electrode portion 23 by the mobile member 222. Therefore, the grasping target is grasped between the first electrode portion 23 and the jaw 42 with the second grasping force F2 greater than the first grasping force F1.

As described above, the movement position changeover button 221 serves as a grasping force converting unit configured to convert a grasping force so that the second grasping force F2 between the first electrode portion 23 and the jaw 42 in the second treatment mode is greater than the first grasping force F1 between the first electrode portion 23 and the jaw 42 in the first treatment mode.

Accordingly, the grasping treatment device 1 having the configuration described above provides the following advantageous effects. In the grasping treatment device 1, the elastic force k0(x0+x3) acts on the movable portion (the movable cylindrical member 46 and the inner pipe 77) from the coil spring 126 in the first treatment mode. In the second treatment mode, the elastic force k0(x0+x3) acts on the movable portion (the movable cylindrical member 46 and the inner pipe 77) from the coil spring 126, and the jaw 42 is pressed toward the first electrode portion 23 by the movement member 222. Therefore, in the second treatment mode, the grasping target is grasped between the first electrode portion 23 and the jaw 42 with the second grasping force F2 greater than the first grasping force F1 in the first treatment mode. Thus, the reformation of the living tissue (grasping target) with the high-frequency current is more accelerated in the second treatment mode than in the first treatment mode. Therefore, the performance of the coagulation of the grasping target with the high-frequency current is improved, so that deterioration in the performance of the coagulation of the grasping target can be prevented in the second treatment mode, which does not use the ultrasonic vibration. Consequently, the grasping target (living tissue) can be stably sealed in the second treatment mode, which does not use the ultrasonic vibration.

OTHER MODIFICATIONS

In the embodiments described above, in the first treatment mode, a high-frequency current is output from the high-frequency current supplier 9, and the high-frequency current is transmitted to the first electrode portion 23 and the second electrode portion 93. However, in the first treatment mode, for example, no high-frequency current may be output from the high-frequency current supplier 9, and no high-frequency current may be transmitted to the first electrode portion 23 and the second electrode portion 93. That is, in the first treatment mode, at least the ultrasonic vibration has only to be generated in the ultrasonic vibrator 12, and at least the ultrasonic vibration has only to be transmitted to the first electrode portion 23. Consequently, a grasping target such as a living tissue is coagulated and cut in the first treatment mode.

In conclusion, according to the present invention, it is only necessary to provide a grasping force converting unit (32, 33, 35; 147; 162; 172; 57B; 221) configured to convert a grasping force so that the second grasping force F2 between the first electrode portion 23 and the jaw 42 in the second treatment mode in which the high-frequency current alone is transmitted to the first electrode portion 23 and the second electrode portion 93 is greater than the first grasping force F1 between the first electrode portion 23 and the jaw 42 in the first treatment mode in which at least the ultrasonic vibration is transmitted to the first electrode portion 23 of the probe 3.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A grasping treatment device comprising:
    a probe which extends along a longitudinal axis, and which is configured to transmit an ultrasonic vibration from a proximal direction to a distal direction, the probe including, in its distal portion, a first electrode portion which functions as an electrode when a high-frequency current is transmitted to the first electrode portion through the probe;
    a jaw configured to open or close relative to the first electrode portion, the jaw including a second electrode portion which functions as an electrode when a high-frequency current is transmitted to the second electrode portion; and
    a grasping force converting unit configured to convert a grasping force between the distal portion of the probe and the jaw,
    the grasping force converting unit including:
        a first movable handle configured to move so as to input a close operation between the jaw and the distal portion of the probe;
        a second movable handle which is different from the first movable handle, and which is configured to move so as to input a close operation between the jaw and the distal portion of the probe;
        a movable portion which is configured to move along the longitudinal axis in response to an input of the close operation by each of the first movable handle and the second movable handle so that the jaw closes relative to the distal portion of the probe, and which is configured to stop after the movable portion moves in response to the input of the close operation by each of the first movable handle and the second movable handle;
        a slider portion which is configured to move together with the movable portion along the longitudinal axis when the movable portion moves in response to the input of the close operation by each of the first movable handle and the second movable handle, and which is configured to move relative to the movable portion along the longitudinal axis when the movable portion stops after moving in response to the input of the close operation by each of the first movable handle and the second movable handle;
        an elastic member which connects between the movable portion and the slider portion, and which is configured to change in a contraction amount thereof in response to a movement of the slider portion relative to the movable portion;
        a first stopper portion on which the first movable handle is configured to abut when the elastic member contracts by a first contraction amount; and
        a second stopper portion on which the second movable handle is configured to abut when the elastic member contracts by a second contraction amount greater than the first contraction amount.

2. The grasping treatment device according to claim 1, wherein the first movable handle and the second movable handle have the same rotation axis,
    the first movable handle is configured to move together with the second movable handle until the first movable handle abuts on the first stopper portion, and
    the second movable handle is configured to move independently from the first movable handle until the second movable handle abuts on the second stopper portion.

3. The grasping treatment device according to claim 1, wherein:
    the first movable handle has a first rotation axis,
    the second movable handle has a second rotation axis different from the first rotation axis, and
    the slider portion includes
        a first slider which is configured to move relative to the movable portion until the elastic member contracts by the first contraction amount by moving the first movable handle until the first movable handle abuts on the first stopper portion, and
        a second slider which is configured to move relative to the movable portion independently from the first slider until the elastic member contracts by the second contraction amount by moving the second movable handle until the second movable handle abuts on the second stopper portion.

4. The grasping treatment device according to claim 1, wherein:
    the first movable handle has a first rotation axis;
    the second movable handle has a second rotation axis different from the first rotation axis.

5. The grasping treatment device comprising:
    a probe which extends along a longitudinal axis, and which is configured to transmit an ultrasonic vibration from a proximal direction to a distal direction, the probe having a distal portion, the distal portion of the probe including a first electrode portion which functions as an electrode when a high-frequency current is transmitted to the first electrode portion through the probe;
    a jaw configured to open or close relative to the first electrode portion, the jaw including a second electrode portion that functions as an electrode when a high-frequency current is transmitted the second electrode portion; and a grasping force converting unit configured to convert a grasping force between the distal portion of the probe and the jaw, the grasping force converting unit including:
- a first movable handle configured to move so as to input a close operation between the jaw and the distal portion of the probe;
- a second movable handle which is different from the first movable handle, and which is configured to move so as to input a close operation between the jaw and the distal portion of the probe;
- a movable portion which is configured to move along the longitudinal axis in response to an input of the close operation by each of the first movable handle and the second movable handle so that the jaw closes relative to the distal portion of the probe, and which is configured to stop after the movable portion moves in response to the input of the close operation by each of the first movable handle and the second movable handle;
- a first slider which is configured to move together with the movable portion along the longitudinal axis when the movable portion moves in response to the input of the close operation by the first movable handle, and which is configured to move relative to the movable portion along the longitudinal axis when the movable portion stops after moving in response to the input of the close operation by the first movable handle;
- a second slider which is configured to move together with the movable portion along the longitudinal axis when the movable portion moves in response to the input of the close operation by the second movable handle, and which is configured to move relative to the movable portion along the longitudinal axis when the movable portion stops after moving in response to the input of the close operation by the second movable handle;
- a first elastic member which connects between the movable portion and the first slider, and which has a first elastic contact, the first elastic member being configured to contract when the first slider moves relative to the movable portion in response to the input of the close operation by the first movable handle; and
- a second elastic member which connects between the movable portion and the second slider, and which has a second elastic contact higher than the first elastic contact, the second elastic member being configured to contract when the second slider moves relative to the movable portion in response to the input of the close operation by the second movable handle.

6. A grasping treatment device comprising:
a probe which extends along a longitudinal axis, and which is configured to transmit an ultrasonic vibration from a proximal direction to a distal direction, the probe having a distal portion that includes a first electrode portion which functions as an electrode when a high-frequency current is transmitted to the first electrode portion through the probe;
a jaw configured to open or close relative to the first electrode portion, the jaw including a second electrode portion which functions as an electrode when a high-frequency current is transmitted to the second electrode portion;
a close operation input portion configured to input a close operation between the jaw and the distal portion of the probe; and
a grasping force converting unit configured to convert a grasping force between the distal portion of the probe and the jaw, the grasping force converting unit including:
- a movable portion which is configured to move along the longitudinal axis in response to an input of the close operation by the close operation input portion so that the jaw closes relative to the distal portion of the probe, and which is configured to stop after the movable portion moves in response to the input of the close operation;
- a slider portion which is configured to move together with the movable portion along the longitudinal axis when the movable portion moves in response to the input of the close operation, and which is configured to move relative to the movable portion along the longitudinal axis when the movable portion stops after moving in response to the input of the close operation;
- a first elastic member which is configured to contract in response to a movement of the slider portion relative to the movable portion when the first elastic member connects between the movable portion and the slider portion;
- a second elastic member which is different from the first elastic member, and which is configured to contract in response to a movement of the slider portion relative to the movable portion when the second elastic member connects between the movable portion and the slider portion; and
- a connection state changeover portion which is configured to change between a first connection state and a second connection state, only the first elastic member being configured to connect between the movable portion and the slider portion in the first connection state, not only the first elastic member but also the second elastic member parallel to the first elastic member being configured to connect between the movable portion and the slider portion in the second connection state.

* * * * *